(12) United States Patent
Kannar et al.

(10) Patent No.: US 8,021,697 B2
(45) Date of Patent: Sep. 20, 2011

(54) SUBSTANCES HAVING BODY MASS REDISTRIBUTION PROPERTIES

(75) Inventors: David Kannar, Belgrave South (AU); Barry James Kitchen, Bon Beach (AU); Richard Stuart Weisinger, Ringwood North (AU)

(73) Assignee: Horizon Science Pty. Ltd., Melbourne, Victoria (AU)

( * ) Notice: Subject to any disclaimer, the term of this patent is extended or adjusted under 35 U.S.C. 154(b) by 660 days.

(21) Appl. No.: 11/915,838

(22) PCT Filed: Jun. 5, 2006

(86) PCT No.: PCT/AU2006/000769
§ 371 (c)(1),
(2), (4) Date: Feb. 27, 2008

(87) PCT Pub. No.: WO2006/128259
PCT Pub. Date: Dec. 7, 2006

(65) Prior Publication Data
US 2008/0200559 A1    Aug. 21, 2008

(30) Foreign Application Priority Data

Jun. 3, 2005   (AU) .............................. 2005902927

(51) Int. Cl.
*A61K 36/00*   (2006.01)
*A61K 47/00*   (2006.01)
(52) U.S. Cl. ......................... 424/725; 424/439; 514/909
(58) Field of Classification Search .................. 424/725, 424/439; 514/909
See application file for complete search history.

(56) References Cited

U.S. PATENT DOCUMENTS

| 2003/0165574 A1 | 9/2003 | Ward et al. |
| 2003/0232763 A1 | 12/2003 | Jia |
| 2004/0001862 A1 | 1/2004 | Xiu |
| 2004/0097429 A1 | 5/2004 | Nieuwenhuizen et al. |

FOREIGN PATENT DOCUMENTS

| JP | 61-69727 | 4/1986 |
| WO | WO01/78629 | 10/2001 |
| WO | WO02/14477 | 2/2002 |
| WO | WO2005/089066 | 9/2005 |

OTHER PUBLICATIONS

Zemel, M., "Regulation of Adiposity and Obesity Risk by Dietary Calcium: Mechanisms and Implications", Journal of the American College of Nutrition, vol. 21, No. 2., 146S-151S, 2002.
Goosens, G.H., et al., "Possible Involvement of the Adipose Tissue Renin-Angiotensin System in the Pathophysiology of Obesity and Obesity-Related Disorders", Obesity Reviews, vol. 4, pp. 43-55, 2003.
Zheng, G. et al., Anti-Obesity Effects of Three Major Components of Green Tea, Catechins, Caffeine and Theanine, in Mice, In Vivo, vol. 18, pp. 55-62, 2004.
Han, L, et al., Anti-Obesity Action of Salix matsudana Leaves (Part 1). Anti-Obesity Action by Polyphenols of Salix Matsudana in High Fat-Diet Treated Rodent Animals, Phytother.Res., vol. 17, pp. 1188-1194, 2003.
Mehra, U.R., et al., "Effect of Restricted and Ad libitum Feeding of Urea Molasses Liquid Diet (UMLD) on the Performance of Adult Crossbred Cattle", AJAS, vol. 11, No. 1, pp. 30-34, 1998.
Kumar, H. et al., "Effect of Long Term Feeding of Urea Molasses Liquid Diet*(UMLD) on Ovarian Activity in Crossbred Heifers", Indian Vet. Med. Jour., vol. 22, pp. 185-188, Sep. 1998.
Rosenberg, M. M. et al., "Response of Growing and Mature Pullets to Continuous Feeding of Cane Final Molasses", Poultry Sci, vol. 35, pp. 292-303, 1956.
Kajimoto, Osami et al., "Tea Catechins with a Galloyl Moiety Reduce Body Weight and Fat", Journal of Health Science, vol. 51, No. 2., pp. 161-171, 2005.
Bray, G. et al., "Current and Potential Drugs for Treatment of Obesity", Endocrine Reviews, vol. 20, No. 6, pp. 805-875, Dec. 1999.
Altukhov et al., 2004, Human Physiol. 30(2):216-223.
Anderson, 2008, Proc. Nutrition Soc. 67:48-53.
Baba et al., 2005, Eur. J. Nutr. 44:1-9.
Badescu et al., 2005, Rom. J. Physiol. 42:1-4.
Balasubramanian et al., 2010, Carcinogenesis 31(3):496-503.
Banini et al., 2006, Nutrition 22:1137-1145.
Basu et al., 2010, J. Nutr. 140:1582-1587.
Bento et al., 1998, Carbohydrate Polymers 37:257-261.
Bento et al., 1997, Intl. Sugar J. 99(1187 Suppl.):555-562.
Bento et al., 1997, SIT Poster #722 Publ. Techn. Papers Proc. Ann. Meet. Sugar Industry Technologiests 56:383-392 "Gel Permeation Chromatography of Sugar Materials Using . . . ".
Berhow et al., 2000, Mutation Res. 448:11-22.
Brown et al., 2009, Br. J. Nutr. 101:886-894.
Burkon et al., 2008, Mol. Nutr. Food Res. 52:549-557.
Chajuss, 2004, "Soy Molasses: Processing and Utilization as a Functional Food," in: Soybeans as Functional Foods and Ingredients, Liu et al., Eds.
Clarke et al., "Polyfructose: A New Microbial Polysaccharide," in: Carbohydrates as Organic Raw Materials, Lichtenthaler, Ed., VCH, Weinheim, 1990.
Coca et al., 2005, Chemosphere 60:1408-1415.
Dal-Pan et al., 2010, BMC Physiol. 10:11.
Dallas et al., 2008, Phytomedicine 15:783-792.
Edye et al., 1998, "The Fate of Soluble Sugarcane Polysaccharides in Sugar Manufacture," Poster.
Fernandes et al., 2009, Talanta 79:222-228.
Frank et al., 2009, J. Nutr. 139:58-62.
Fujita et al., 2000, Abstract AGFD-086, Book of Abstracts, 219th ACS National Meeting, San Francisco, CA, Amer. Chem. Soc., Washington, DC.

(Continued)

Primary Examiner — Kevin E Weddington
(74) Attorney, Agent, or Firm — Dilworth Paxson, LLP; Gary D. Colby

(57) ABSTRACT

There is provided a method for altering the distribution of body mass by altering the distribution of body mass by decreasing overall percentage fat and/or increasing the proportion of lean mass to fat mass comprising administering to a subject one or more compounds having the ability to alter body mass composition and/or ACE inhibiting activity or a physiologically acceptable derivative or prodrug thereof.

10 Claims, 12 Drawing Sheets

OTHER PUBLICATIONS

Fukino et al., 2008, Eur. J. Clin. Nutr. 62:953-960.
Fukino et al., 2005, J. Nutr. Sci. Vitaminol. 51:335-342.
Hangyal, 1969, Cukoripar 22(5):183-186 (Abstract only; HCAPLUS database record No. 1970:123241).
Hatano et al., 2008, Chemosphere 71:1730-1737.
Hollis et al., 2009, J. Amer. Coll. Nutr. 28(5):574-582.
Islam, 2008, Z. Naturforsch. 63c:233-240.
Jacome et al., 2009, Alim. Nutr. 20(2):185-190.
Kantachote, 2009, Electr. J. Biotechnol. 12(3):12.
Khan et al., 2010, J. Exp. Biol. 61(15):4185-4196.
Kita et al., 2004, BioFactors 22:259-263.
Kovacs et al., 2004, Br. J. Nutr. 91:431-437.
Loke et al., 2010, Arterioscler. Thromb. Vasc. Biol. 30:749-757.
Machowetz et al., 2008, Horm. Metab. Res. 40:697-701.
Mantovani et al., 2008, Nutrition 24:305-313.
Mantovani et al., 2006, Cancer Epidemiol. Biomarkers Prev. 15:1030-1034.
Mantovani et al., 2004, Cancer Epidemiol. Biomarkers Prev. 13(10):1651-1659.
Nagasako-Akazome et al., 2007, J. Oleo Sci. 56(8):417-428.
Ochiai et al., 2009, Hypertension Res. 32:969-974.
Olthof et al., 2000, "Metabolism of Chlorogenic Acid, Querctein-3-rutinoside and . . . " In: Spec. Publ. Royal Soc. Chem: 255 Dietary Anticarcinogens and Antimutagens, pp. 73-75.
Onimawo et al., 2010, African J. Food Agric. Nutr. Develop. 10(5):1-17.
Palfi et al., 2009, J. Nutr. Biochem. 20:418-425.
Pena et al., 2003, Chemosphere 51:893-900.
Qu et al., 2007, J. Clin. Rehabil. Tiss. Eng. Res. 11(43):8805-8808.
Schoen et al., 2009, Nutrition 25:499-505.
Shore et al., 1984, Sugar Technol. Rev. 12:1-99.
Simonetti et al., 2001, Meth. Enzymol. 335:122-130.
Stracke et al., 2010, Eur. J. Nutr. 49:301-310.
Tominaga et al., 2006, J. Health Sci. 52(6):672-683.
Vercellotti et al., 1998, Membrane Separation Chemistry in Sugar Processing Applications, Proceedings of the Conference on Sugar Processing Research, Savannah, GA, pp. 248-228.
Vercellotti et al., 1998, SIT Paper 727, Sugar Industry Technologist Annual Meeting, Marseille France, pp. 49-78.
Vercellotti et al., 1996, Proc. Conf. Sugar Processing Res., SPRI, New Orleans, 321-349.
Wachowicz, 1978, Gazeta Cukrownicza 86:125-127 (Abstract Only; HCAPLUS database record No. 1978:548469).
Wang et al., 2008, Carbohydrate Polymers 74:127-132.
Winter et al., 1992, J. Exp. Mar. Biol. Ecol., 155:263-277.
Wu et al., 2005, Carcinogenesis 26(5):976-980.
Wu et al., 2002, Huanjing Wuran Yu Fangzhi 24(1):13-18 (Abstract Only; HCAPLUS database record No. 2002:439963).
Zhang et al., 2007, Can. J. Physiol. Pharmacol. 85:1116-1123.
Zielinska-Przyjemska et al., 2007 Acta Sci. Pol., Technol. Aliment. 6(3):75-87.
Zhang et al., 2009, Zhongguo Difangbingxue Zazhi 28(4):381-385 (Abstract Only).
Nagao et al., 2009, Jap. Pharmacol. Therapeut. 37(4):333-344 (Abstract Only).
Ishikura et al., 2008, Jap. Pharmacol. Therapeut. 36(10):931-939 (Abstract Only).
Lee et al., 2008, Hanguk Kikpum Yongyang Kwahak Hoechi 37(5):561-570 (Abstract Only).
Nakamura et al., 2008, Jap. Pharmacol. Therapeut. 36(4):347-357 (Abstract Only).
Hu et al., 2006, Zhongguo Linchuang Kangfu 10(43):79-81 (Abstract Only).
Melby et al., 2007, Daizu Tanpakushitsu Kenkyu 9:138-146 (Abstract Only).
Nakamura et al., 2007, Jap. Pharmacol. Therapeut. 35(6):661-671 (Abstract Only).
Zielinska-Przyjemska et al., 2005, Polski Merkuriusz 19(109):41-47 (Abstract Only).
Kishihara et al., 1986, Kagaku Kogaku Ronbunshu 12(2):199-205 (Abstract Only).

SUBSTANCES HAVING BODY MASS REDISTRIBUTION PROPERTIES

This application is a national phase application of International Application Ser. No. PCT/AU2006/000769, filed Jun. 5, 2006, which claims priority to Australian application Serial No. AU 2005 902927 filed Jun. 3, 2005.

FIELD OF THE INVENTION

The invention relates to therapeutic formulations and methods for altering body mass distribution. More specifically the invention relates to therapeutic formulations comprising compounds, such as flavonoids, polyphenols, polypeptides, leucine and other branched chain amino acids and dairy bioactives, for use in methods for altering body mass distribution.

BACKGROUND OF THE INVENTION

In this specification where a document, act or item of knowledge is referred to or discussed, this reference or discussion is not an admission that the document, act or item of knowledge or any combination thereof was at the priority date, publicly available, known to the public, part of common general knowledge; or known to be relevant to an attempt to solve any problem with which this specification is concerned.

Increasing Lean Body Mass

There are a number of diseases which involve cachexia (weakness and wasting of the body) as a symptom in which the body loses significant amounts of lean body mass. Examples of such diseases include diabetes, cancer, Alzheimers, bulimia nervosa and anorexia.

There is thus a need for a treatment which enables the body to increase its percentage of lean body mass with a minimal increase, or ideally a decrease, in the percentage of fat mass.

Polyphenols

Polyphenols (compounds with two or more phenolic hydroxy groups) are a class of phytochemicals found in a variety of sources including wine, grapes, cocoa and sugar cane. Polyphenols (or phenolics) all have a common basic chemical component, that is, a phenolic ring structure. There are at least 8000 identified polyphenols in a number of sub-categories, such as anthocyanins and catechins. Natural polyphenols can range from simple molecules such as phenolic acid to large highly polymerized compounds such as tannins. Conjugated forms of polyphenols are the most common, where various sugar molecules, organic acids and lipids (fats) are linked with the phenolic ring structure. Differences in this conjugated chemical structure account for different chemical classifications and variation in the modes of action and health properties of the various compounds.

Polyphenols are considered to have a number of health benefits including:
  antioxidant activity;
  cancer preventative properties;
  heart disease and hypertension protection;
  antibiotic/antiviral activity;
  anti-inflammatory activity;
  ophthamological properties; and
  protecting and strengthening blood vessels.

Polyphenols are responsible for the brightly colored pigments of many fruits, vegetables and flowers (ranging from pink through scarlet, purple and blue), they protect plants from diseases and ultraviolet light and help prevent damage to seeds until they germinate.

Unfortunately, although the epidemiologic data for regular fruit and vegetable intake and disease prevention is strong, dietary supplements containing isolated phenolic antioxidants have not been extensively studied in terms of disease prevention. Products such as green tea, HCA (hyroxycitric acid) and inulin claim weight loss benefits based on the assumption that these products delay glucose absorption and/or regulate insulin to control appetite. This has yet to be proven in controlled clinical trials with humans (*Functional Food Update* 01, National Centre of Excellence in Functional Foods, Australia. June 2006).

Sugar Cane

Anthocyanins are polyphenolic flavylium salts with sugar units attached to the molecule and are derived chiefly from six anthocyanidins: pelargonidin, cyanidin, delphinidin, peonidin, petunidin and malvidin. These compounds differ in the position and number of hydroxyl groups in ring B but all have a sugar unit at the 3 position and are water soluble. With the exception of the petunidin group, representatives of all other anthocyanin classes have been located in sugar cane.

The basic structure common to all anthocyanins is as follows:

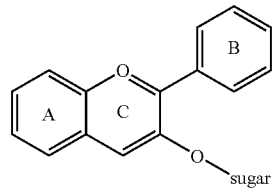

Tea

Second only to water, tea is one of the most widely consumed beverages in the world. Approximately 3.0 million metric tons of dried tea is produced annually, 20% of which is green tea, 2% is oolong and the remainder is black tea (International tea committee Annual bulletin of statistics 2002). Black, oolong and green tea are produced from the leaves of the tea plant *Caimellia sinensis*, a member of the Theaceae family. Different varieties of tea are produced by varying the degree of leaf oxidation. Green tea is produced by steaming freshly harvested leaves at high temperatures, inactivating oxidative enzymes. This preserves the high polyphenol content found in green tea. Black tea leaves are the most oxidated, while oxidation of oolong tea leaves is midway between green tea and black tea.

The majority of polyphenols in tea are flavonols, specifically catechins. These small molecules react with one another during the oxidation process that produces black and oolong teas to form larger, highly colorful compounds called theaflavins and thearubigins.

There has recently been a lot of research into potential pharmaceutical benefits of the polyphenols extracted from tea. The most potent chemopreventive agent commonly extracted from tea is (−)-epigallocatechin-3-gallate (EGCG). There are also claims that green tea polyphenols can assist with weight loss because of its ability to increase metabolism and fat burning noted whilst studying the effect of polyphenols on cholesterol levels in the blood. Medicines made from tea polyphenols have become part of the treatment for nephritis, chronic hepatitis, and leukemia in China. In other countries, green tea supplements are available.

The basic structure common to all catechins is as follows:

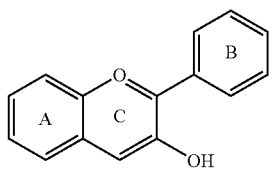

Cocoa

Theobroma cocoa is a rich source of flavonoids including polyphenols. One study on the consumption of dark chocolate by humans has shown that flavonoid rich chocolate improves endothelial function and increases plasma epicatechin concentrations. However, that study found no change in oxidative stress measures, lipid profiles, blood pressure, body weight or body mass index [Engler et al, "Flavonoid-rich dark chocolate improves endothelial function and increases plasma epicatechin concentrations in healthy adults" *J Am Coll Nutr* 2004; 23(3):197-204].

Another study on the consumption of dark chocolate found no changes in the total antioxidant capacity of plasma or in the oxidation susceptibility of serum lipids. The study did find that cocoa polyphenols may increase the concentration of HDL cholesterol whereas chocolate fatty acids may modify the fatty acid composition of LDL and make it more resistant to oxidative damage [Mursu et al "Dark chocolate consumption increases HDL cholesterol concentration and chocolate fatty acids may inhibit lipid peroxidation in healthy humans" *Free Radic Biol Med* 2004 Nov. 1; 37(9):1351-9].

ACE Inhibitors

ACE is an important part of the renin-angiotensin-aldosterone system, one of the major endocrine systems in the body. ACE cleaves angiotensin I (ANG-I) to the potent vasoconstrictor angiotensin II (ANG-II) which regulates major physiological functions of the body including blood pressure, body sodium and fluid homeostasis which mediates its function via cellular receptors AT-1 and AT-2. ACE inhibitors have been demonstrated to be useful in lowering blood pressure and in the treatment of left ventricular dysfunction and diabetic neuropathy.

There have been a number of studies into the various roles of ANG-II:

organogenesis (Oliverio M I, Madsen K, Best C F, Ito M, Maeda N, Smithies O, Coffinan T M. "Renal growth and development in mice lacking AT1A receptors for angiotensin II". *Am. J. Physiol.* 1998;274:F43-F50);

formation of pre-adipocytes;

human preadipocytes express a high affinity for AT-1 receptor substypes (Crandall D L, Armellino D C, Busler D E, McHendry-Rinde B, Kral J G. "Angiotensin II receptors in human preadipocytes: role in cell cycle regulation". *Endocrinology* 1999;140:154-158);

white adipose tissue has been reported to be an important site of angiotensinogen production (Cassis L A, Saye J, Peach M J. "Location and development of rat angiotensin messenger RNA". 1988; *Hypertension* 11:591-596);

stimulate adipogenesis or formation of adipose (fat) cells (Darimont C, Vassaux G, Alihaud G, Negrel R. "Differentiation of preadipose cells: paracrine role of prostacyclin upon stimulation of adipose cells by angiotensin-II". *Endocrinology* 1994;135:2030-2036; Saint-Marc P. Kozak L P, Ailhaud G, Darimont C, Negrel R. "Angio-tensin-II as a trophic factor of white adipose tissue: stimulation of adipose cell formation". *Endocrinology* 2001;142:487-492);

increase lipogenesis and triglyceride accumulation in preadipose cells and human adipocytes (Jones B H, Standridge M K, Moustaid N. "Angiotensin-II increases lipogenesis in 3T3-L1 and human adipose cells". *Endocrinology* 1997;138:1512-1519);

rats treated with an ACE inhibitor (losartan) exhibit a reduction in adipocyte size (Zorad S, Fickova M, Zelezna B, Macho L, Kral J G. "The role of angiotensin-II and its receptors in regulation of adipose tissue metabolism and cellularity". *Gen. Physiol. Biophys.* 1995;14:383-391)

Collectively, these studies indicate that ANG-II plays an important role in the development of adipose tissue.

Studies have also shown that ACE inhibitors may be useful in reducing weight gain.

In angiotensinogen deficient mice, weight gain is lower than in normal wild type mice despite food intake being similar for both genotypes (Massiera F, Seydoux J, Geloen A, Quignard_Boulange A, Turban S, Saint-Marc P, Fukamizu A, Negrel R, Ailhaud G. and Teboul M. "Angiotensinogen-Deficient mice exhibit impairment of diet-induced weight gain with alteration in adipose tissue development and increase in locomotor activity". *Endocrinology* 2001;142(12):5220-5225).

Overfeeding of rodents leads to increased production of ANG-II and chronic ANG-II infusion results in a dose dependant reduction in body weight (Cassis L A, Marshall D E, Fettinger M J, Rosenbluth B, Lodder R A. "Mechanisms contributing to angiotensin II regulation of body weight". *Am. J. Physiol. Endocrinol. Metab.* 1998;274:E867-E876).

In obese human hypertensive patients, ANG-II increases in adipocytes and may be a contributing factor in the development of insulin resistance. This may be aggravated by the inhibition of preadipocyte recruitment, which results in redistribution of fat to the liver and skeletal muscle. For this reason, ACE-inhibition may have potential in slowing the development of type 2 diabetes and pathophysiological roles of the adipose-tissue renin-angiotensin-receptor system in metabolic syndrome (Engeli S, Schling P, Gorzelniak K, Boschmann M, Janke J, Ailhaud G, Teboul M, Massiera F, Sharma A M. "The adipose-tissue renin-angiotensin-aldosterone system: role in metabolic syndrome". *The International Journal of Biochemistry & Cell Biology* 2003;35:807-825.)

However, none of these studies disclose a method for changing body mass composition, eg, a reduced fat mass and increased lean muscle mass. Increasing lean body mass is not necessarily associated with a weight loss. There is thus still a need for such a method to assist subjects suffering from cachexia.

Dairy Bioactives, Leucine, ACE Inhibitory Peptides and Other Branched Chain Amino Acids Milk bioactives, leucine and other branched chain amino acids are natural angiotensin converting enzyme (ACE) inhibitors. ACE inhibitory peptides may be released by proteolysis of milk proteins by lactic acid bacterial during cheese ripening. They may also be isolated from milk and whey during fermentation (Fitzgerald R J, Murray B A. "Bioactive Peptides and lactic fermentations". *International Journal of Dairy Technology* 2006;59(2):118-125). ACE inhibitory dairy peptides have an $IC_{50}$ values >520 μm and sufficient amounts may be delivered via fermented milks and extracts of fermented dairy products. Although weight reduction has been proposed using dairy products (Zemel M B et al. "Dairy augmentation of total and central fat loss in obese subjects". *Int. J. Obes. Relat. Metab. Disord.* 2005;29(4):391-7), the role in weight management has recently been questioned (Gunther C W et al. "Dairy products do not lead to alterations in body weight or fat mass in young women in a 1-y intervention". *Am. J. Clin. Nutr.* 2005;81:751-756).

Obesity

A method for increasing the proportion of lean body mass could also be useful for treating subjects suffering obesity.

Every person has and needs fat tissue in their body. When there is too much body fat, the result is obesity. There are over 300 million obese adults, according to the World Health Organization and 1.1 billion overweight people worldwide.

The number of overweight and obese Americans has continued to increase since 1960, a trend that is not slowing down. More than half of US adults are overweight (64.5 percent) and nearly one-third (30.5 percent) are obese. Each year, obesity causes at least 300,000 excess deaths in the U.S., the and healthcare costs of American adults with obesity amount to approximately $100 billion. It is the second leading cause of preventable death after smoking.

Obesity increases one's risk of developing conditions such as high blood pressure, diabetes (type 2), heart disease, stroke, gallbladder disease and cancer of the breast, prostate and colon. The tendency toward obesity is fostered by our environment: lack of physical activity combined with high-calorie, low-cost foods. If maintained, even weight losses as small as 10 percent of body weight can improve one's health.

Being obese and being overweight are not the same condition. Your bathroom scale may give you a measure of your weight and help you follow changes in your weight, but it is not the best way to determine if you are overweight or obese, or at risk for developing obesity and its related health conditions.

In order to determine whether a person is obese, both body mass index (BMI) and waist circumference is needed. You can have a BMI that indicates you have a healthy weight, but still have a waist measurement above the healthy range.

BMI: is a number based on both height and weight. It can help to determine the degree to which a person may be overweight and gives a reasonable assessment of total body fat for the general population. BMI correlates better with health conditions like heart disease and type 2 diabetes than does weight itself. BMI is not perfect. Some people, like athletes, may measure a high BMI but have more muscle than fat. BMI "cutpoints" are numbers used to help you determine if you are at a healthy weight, overweight, obese or severely obese. It is important to note that BMI is different to Health/Weight tables.

18.5 to 24.9=Healthy Weight
25 to 29.9=Over-weight
30 to 34.9=Obesity (class 1)
35 to 39.9=Obesity (class 2)
40 or more=Severe Obesity (class 3)

Waist circumference measurement is used to determine health risks related specifically to abdominal fat.

For Men: 40 inches or more
For Women: 35 inches or more

If your waist measurement is more than that listed above, and your BMI is between 25 and 34.9, you have an increased risk of developing type 2 diabetes, hypertension and cardiovascular disease.

Causes of Obesity

There are many factors that contribute to causing obesity including genetics, the environment and behaviour.

Genes: Some individuals have a genetic tendency to gain weight and store fat. Although not everyone with this tendency will become obese, some persons without genetic predisposition do become obese. Several genes have been identified as contributors to obesity, and researchers are constructing a Human Obesity Gene Map to identify genetic targets in humans that may lead to the development of new treatments.

Environment: An environment that promotes healthy weight is one that encourages consumption of nutritious foods in reasonable portions and regular physical activity. A healthy environment is important for all individuals to prevent and treat obesity and maintain weight loss. Identifying and consciously avoiding high-risk situations in the environment can assist in weight control efforts.

Behaviour: Adopting healthy habits for lifelong weight control include regular physical activity and nutritious eating. Specific behavioural strategies for weight loss and maintenance include: logging and tracking diet and exercise patterns in a diary, eating a low calorie diet, limiting the amount of calories from fat, expending calories routinely through exercise, monitoring weight regularly, setting realistic goals, and developing a social support network.

The number of obese people in the world is increasing despite the above knowledge. There is thus a need for methods to modify body mass distribution.

SUMMARY OF THE INVENTION

It has surprisingly been found that some compounds will alter the body's food processing to such an extent that the overall body mass distribution is altered. In particular, the addition of these compounds to food results in an increased proportion of lean mass to fat mass when compared to the consumption of the same food without the addition of these compounds. In other words, these compounds can reduce the amount of fat which is produced from consumed food. These body mass altering compounds include polyphenols and milk bioactives.

It has also been found that flavonoids and polyphenols may have ACE inhibiting activity Without wishing to be bound by theory, it is thought that the ACE inhibiting activity is related to the ability of these compounds to alter body mass composition. However, it is acknowledged that the ability of these compounds to alter body mass composition may also be related to antioxidant properties (ie polyphenols) and/or calcium influx effects (ie milk proteins).

According to a first aspect of the invention there is provided a method for altering the distribution of body mass by decreasing overall percentage fat and/or increasing the proportion of lean mass to fat mass comprising administering to a subject an effective amount of one or more compounds having at least one hydroxyl group and the ability to alter body mass composition or a physiologically acceptable derivative or prodrug thereof.

The first aspect of the invention also provides a method comprising administering to a subject a therapeutic formulation comprising an effective amount of one or more compounds having at least one hydroxyl group and the ability to alter body mass composition or a physiologically acceptable derivative or prodrug thereof and an acceptable carrier.

The first aspect of the invention also provides a therapeutic formulation when used to alter the distribution of body mass by decreasing overall percentage fat and/or increasing the proportion of lean mass to fat mass comprising an effective amount of one or more compounds having at least one hydroxyl group and the ability to alter body mass composition or a physiologically acceptable analogue, derivative or prodrug thereof and an acceptable carrier.

The first aspect of the invention also provides for the use of an effective amount of one or more compounds having at least one hydroxyl group and the ability to alter body mass composition or a physiologically acceptable analogue, derivative or prodrug thereof together with a suitable carrier in the manufacture of a medicament for altering the distribution of body mass by decreasing overall percentage fat and/or increasing the proportion of lean mass to fat mass.

In this specification, the term "compounds having at least one hydroxyl group and the ability to alter body mass composition" refers to any compound that contains a hydroxyl group which alters body mass composition by decreasing percentage fat and/or increasing the proportion of lean mass to fat mass. The compounds may be sourced naturally from animals or plants or be manufactured synthetically. An example of an animal source is snake venom which contains peptides. Examples of plant sources are polyphenols from green tea, wine, cocoa, sugar cane, sugar beet, sugar cane and sugar beet waste products, molasses and Chinese herbs such as *Magnolia liliflora* and *Magnolia officinalis*. Other examples of such compounds include (i) flavonoids such as anthocyanins, catechins, polyphenols, chalcones, flavonols, flavones and (ii) polypeptides, leucine and other branched chain amino acids and dairy bioactives such as extracts of whey. Preferably, the compound having at least one hydroxyl group and the ability to alter body mass composition is selected from the group consisting of flavonoids, polyphenols, milk proteins, ACE inhibitory peptides, molasses, molasses extracts, high phenolic sugars and mixtures thereof.

According to a second aspect of the invention there is provided a method for altering the distribution of body mass by decreasing overall percentage fat and/or increasing the proportion of lean mass to fat mass comprising administering to a subject an effective amount of one or more compounds having ACE inhibiting activity or a physiologically acceptable derivative or prodrug thereof.

The second aspect of the invention also provides a method comprises administering to a subject a therapeutic formulation comprising an effective amount of one or more compounds having ACE inhibiting activity or a physiologically acceptable derivative or prodrug thereof and an acceptable carrier.

The second aspect of the invention also provides a therapeutic formulation when used to alter the distribution of body mass by decreasing overall percentage fat and/or increasing the proportion of lean mass to fat mass comprising an effective amount of one or more compounds having ACE inhibiting activity or a physiologically acceptable analogue, derivative or prodrug thereof and an acceptable carrier.

The second aspect of the invention also provides for the use of an effective amount of one or more compounds having ACE inhibiting activity or a physiologically acceptable analogue, derivative or prodrug thereof together with a suitable carrier in the manufacture of a medicament for altering the distribution of body mass by decreasing overall percentage fat and/or increasing the proportion of lean mass to fat mass.

In this specification, the term "compounds having ACE inhibiting activity" refers to any compounds having ACE inhibiting properties and the ability to alter body mass composition by decreasing percentage fat and/or increasing the proportion of lean mass to fat mass. The compounds may be sourced naturally from animals or plants or be manufactured synthetically. An example of an animal source is snake venom which contains peptides. Examples of plant sources are polyphenols from cocoa, sugar cane, sugar beet, sugar cane and sugar beet waste products, molasses, grapes, wine, fruit (berries, drupes, pomes, tropical fruits, juices), vegetables (bulbs, roots, tubers, leaves, stems), herbs, spices, beans, pulses, grains (barley, buckwheat, corn, millets, oats, rice, rye, sorghum, wheat), nuts (almonds, betel nuts, cashews, hazelnuts, peanuts, pecans, walnuts), oilseeds, plant oils, tea, coffee, beer, cider, seeds, green tea, Chinese herbs such as *Magnolia liliflora* and *Magnolia officinalis* and mixtures thereof. Other examples of such compounds include (i) flavonoids such as anthocyanins, catechins, polyphenols, chalcones, flavonols, flavones and (ii) polypeptides, leucine and other branched chain amino acids and dairy bioactives such as extracts of whey. Preferably, the compound having ACE inhibiting properties is selected from the group consisting of flavonoids, polyphenols, milk proteins, cocoa, cocoa products, cocoa extracts, grape extracts, molasses, molasses extracts, high phenolic sugar and mixtures thereof.

According to a third aspect of the invention there is provided a method for altering the distribution of body mass by decreasing overall percentage fat and/or increasing the proportion of lean mass to fat mass comprising administering to a subject an effective amount of one or more polyphenols or a physiologically acceptable derivative or prodrug thereof.

The third aspect of the invention also provides a method comprising administering to a subject a therapeutic formulation comprising an effective amount of one or more polyphenols or a physiologically acceptable derivative or prodrug thereof and an acceptable carrier.

The third aspect of the invention also provides a therapeutic formulation when used to alter the distribution of body mass by decreasing overall percentage fat and/or increasing the proportion of lean mass to fat mass comprising an effective amount of one or more polyphenols or a physiologically acceptable analogue, derivative or prodrug thereof and an acceptable carrier.

The third aspect of the invention also provides for the use of an effective amount of one or more polyphenols or a physiologically acceptable analogue, derivative or prodrug thereof together with a suitable carrier in the manufacture of a medicament for altering the distribution of body mass by decreasing overall percentage fat and/or increasing the proportion of lean mass to fat mass.

In this specification, the term "polyphenols" refers to any polyphenols sourced or derived from cocoa, sugar cane, sugar beet, sugar cane and sugar beet waste products, molasses, grapes, wine, fruit (berries, drupes, pomes, tropical fruits, juices), vegetables (bulbs, roots, tubers, leaves, stems), herbs, spices, beans, pulses, grains (barley, buckwheat, corn, millets, oats, rice, rye, sorghum, wheat), nuts (almonds, betel nuts, cashews, hazelnuts, peanuts, pecans, walnuts), oilseeds, plant oils, tea, coffee, beer, cider, seeds, green tea, Chinese herbs such as *Magnolia liliflora* and *Magnolia officinalis* and mixtures thereof. Preferably, the polyphenol is sourced from molasses, molasses extracts, high phenolic sugar and mixtures thereof. Preferably, the polyphenols have a high antioxidant activity.

According to a fourth aspect of the invention there is provided a method for altering the distribution of body mass by decreasing overall percentage fat and/or increasing the proportion of lean mass to fat mass comprising administering to a subject an effective amount of molasses or an extract thereof.

The fourth aspect of the invention also provides a method comprising administering to a subject a therapeutic formulation comprising an effective amount of molasses or an extract thereof and an acceptable carrier.

The fourth aspect of the invention also provides a therapeutic formulation when used to alter the distribution of body mass by decreasing overall percentage fat and/or increasing the proportion of lean mass to fat mass comprising an effective amount of molasses or an extract thereof and an acceptable carrier.

The fourth aspect of the invention also provides for the use of an effective amount of molasses or an extract thereof together with a suitable carrier in the manufacture of a medicament for altering the distribution of body mass by decreasing overall percentage fat and/or increasing the proportion of lean mass to fat mass.

The term "effective amount" is used herein to refer to an amount which is sufficient to alter the distribution of body mass by increasing lean mass or decreasing fat mass. The proportion of lean mass to fat mass is increased when either the amount of lean mass of a subject increases or the amount of fat mass of a subject decreases. Note that a change in the proportion of lean mass to fat mass does necessarily involve a change in overall weight. An example of an effective amount for animals is 1 to 2% of the diet. Assuming that a human normally consumes 1000 g of food per day and the normal consumption of polyphenols is 1 g/day, the effective amount is likely to be in the range from 2 to 20 mg/day, more preferably 2 to 10 g/day.

The ability of a compound to decrease percentage fat and/or increase the proportion of lean mass to fat mass can be tested using the mice experiment discussed in the examples. If a statistically significant change is obtained when compared to the control then the compound can be used in the invention. A typical result in the mice experiment is a decrease in percentage fat of 8 to 12% or an increase in the proportion of lean mass to fat mass of 4 to 7%. For humans suffering cachexia, an increase in the proportion of lean mass to fat mass of at least 1 to 2% would be ideal.

The term "therapeutic formulation" is a broad term which includes enteral and parenteral pharmaceutical preparations, nutraceuticals, supplements, functional foods and herbal preparations. Examples of suitable formulations include tablets, powders, chewable tablets, capsules, oral suspensions, suspensions, emulsions or fluids, children's formulations, enteral feeds, nutraceuticals, suppositories, nasal sprays, drinks and food products. The carrier may contain any suitable excipients such as starch or polymeric binders, sweeteners, coloring agents, emulsifiers and coatings. Preferably, the carrier is a food product or food ingredient such as sugar or chocolate.

The therapeutic formulation may be in any form appropriate for administration to the subject. The therapeutic formulation may be administered topically, orally or by any other route of administration.

The term "subject" as used herein refers to an animal. There is no limitation on the type of animal that could benefit from the presently described formulations and methods. Preferably, the subject is a mammal and more preferably a human. An "animal" also includes livestock species such as cattle, horses, sheep, pigs, goats, donkeys and poultry birds such as chickens, ducks, turkeys and geese or domestic animals such as cats and dogs. A subject, regardless of whether a human or non-human animal, may also be referred to as an individual, animal, patient, host or recipient. The formulations and methods of the present invention have applications in human medicine, the cosmetic and aesthetic industries, veterinary medicine as well as in general, domestic and wild animal husbandry.

DRAWINGS

Various embodiments/aspects of the invention will now be described with reference to the following drawings in which (asterixes highlight significant differences):

Figure 19:
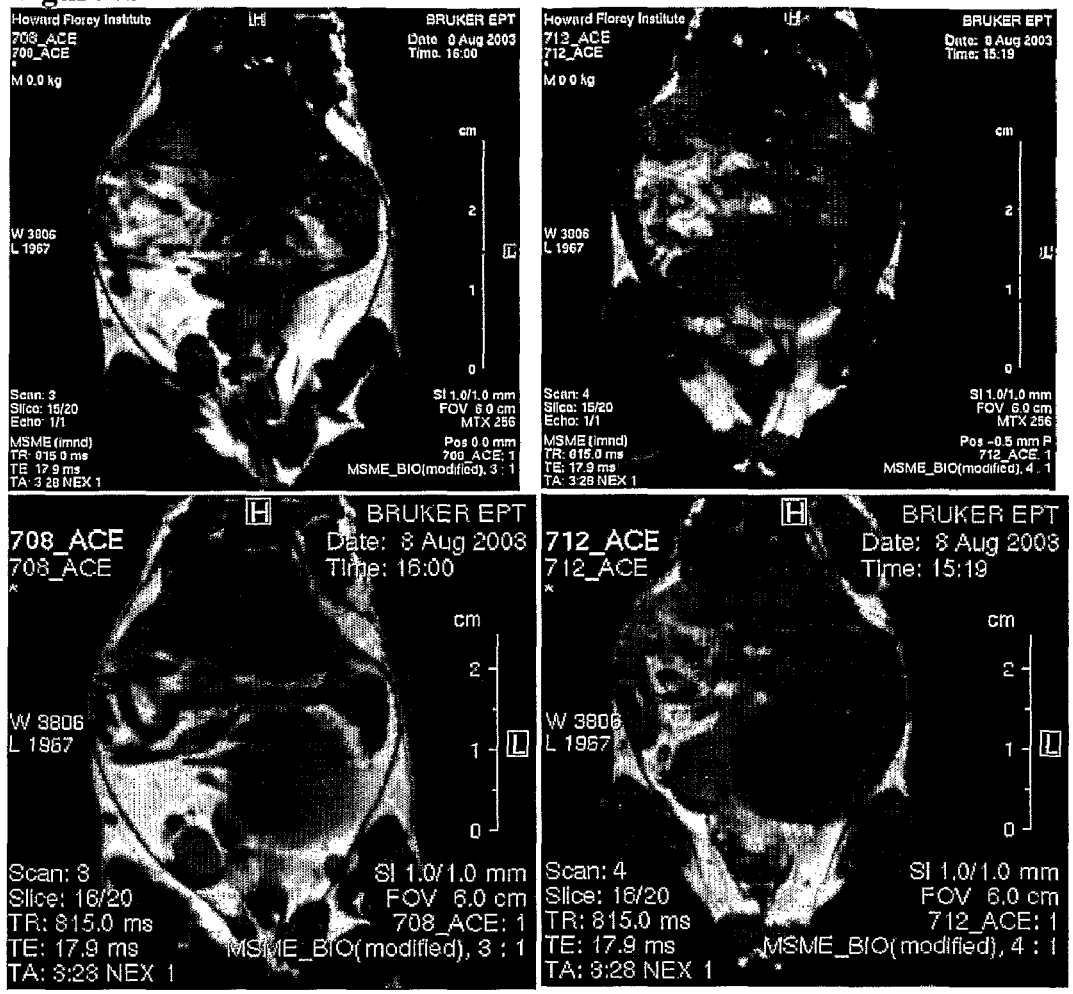

FIG. 19 shows the proton density weighted axial MRI images across the body of ACE +/+ (A) and for ACE −/− mice (B). Bright, white areas denote fat. Each series of images represents data from a single animal. White arrowhead indicates android fat.

Figure 20:
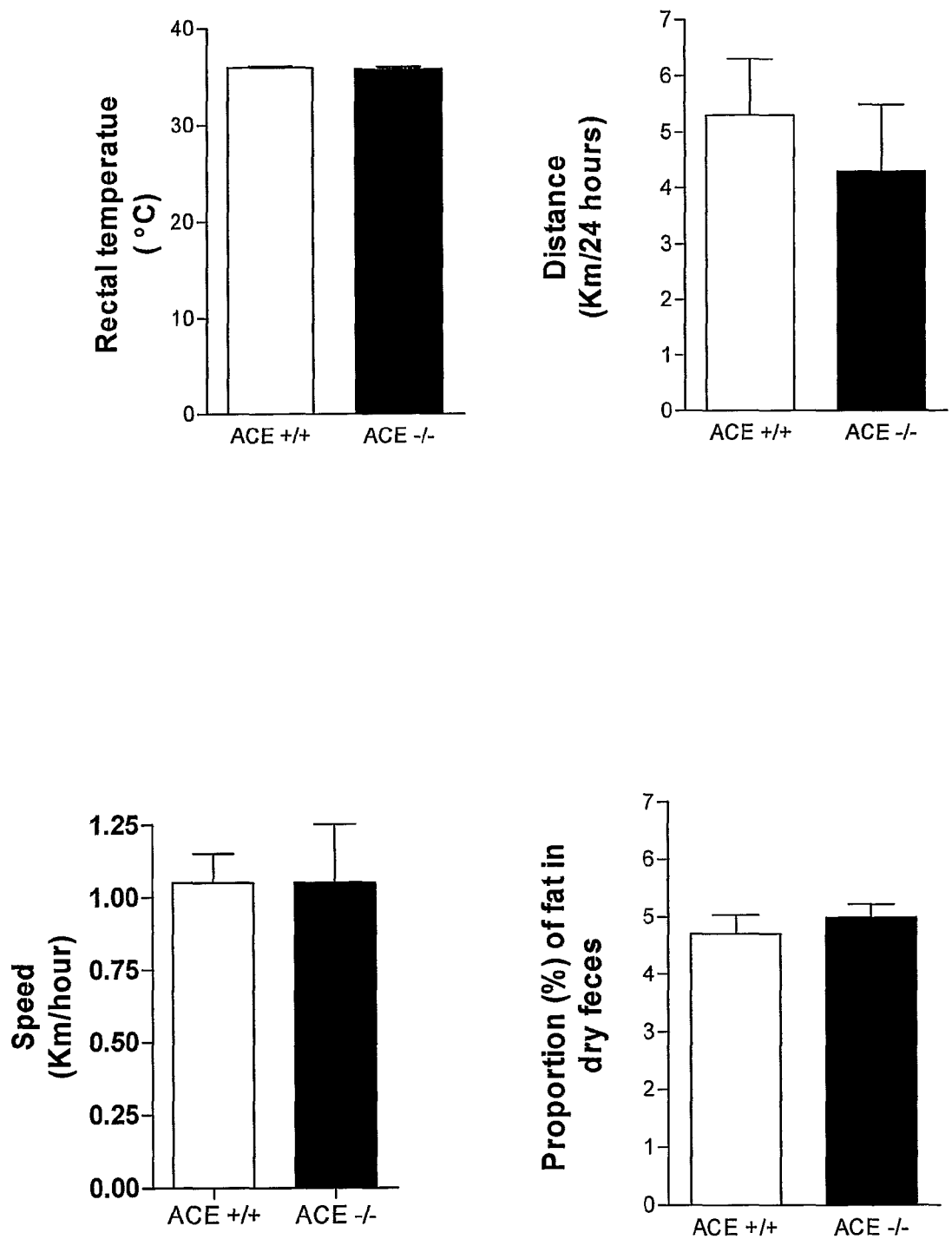

FIG. 20 shows the rectal temperature (A) Spontaneous running wheel activity (Distance run per day (B), speed (C) and proportion of fat in the fecal matter (D) in ACE +/+ (Empty bars) and ACE −/− mice (filled bars). The values are mean±SEM (n=5 per group for rectal temperature, spontaneous running wheel activity measurements. ACE (−/−): n=6 and ACE (+/+): n=7 for fecal fat analysis).

EXAMPLES

Various embodiments of the invention will now be described with reference to the following non-limiting examples.

Example 1

This example compares the phenolic content and antioxidant activities of phenolic powders which may be used in the methods of the invention.

Methods

The phenolic content and antioxidant activities of three phenolic powders, the molasses phenolic powder produced at IFT (International Food Technology Company), Hansen's Grape Extract HW 65-10 phenolic powder, and the Vinlife™ grape seed extract powder, were compared. The powders were dissolved in 80% methanol at a concentration of 5 mg/ml. Further dilution with water was required to achieve concentrations appropriate for the respective assays. The results of these assays are shown in Table 1 (below).

Results

The data in Table 1 allows the relative antioxidant efficiency of the powders to be compared. Table 2 shows the specific activities of the three powders, i.e. the number of antioxidant units per phenolic unit.

TABLE 1

Phenolic content and antioxidant activity of three phenolic powders

| Powder | Phenolic Content (mg catechin eqs/gram) | Antioxidant Content (mg gallic acid eqs/gram) |
|---|---|---|
| Molasses powder | 254 | 32.2 |
| Hansen's HW 65-10 Grape Extract | 775 | 144 |
| Vinlife Grape Seed Extract | 533 | 105 |

TABLE 2

Specific antioxidant activity of three phenolic powders

| Powder | Specific Activity (gallic acid eqs/catechin eqs) |
|---|---|
| Molasses powder | 0.127 |
| Hansen's HW 65-10 Grape Extract | 0.188 |
| Vinlife ™ Grape Seed Extract | 0.197 |

Discussion

These results show that the molasses powder has a lower content of phenolics than the other 2 powders and a lower specific antioxidant activity. This is likely due to differences in the phenolic profiles between the various powders. HPLC analysis suggests that the molasses powder does not contain many of the simple phenolic acids, such as gallic acid, which are very powerful antioxidants. These compounds appear to be insufficiently hydrophobic to bind to the XAD 16 resin. However, different extraction methods are likely to be able to extract such smaller hydrophilic compounds and they may be included into a molasses extract for use in a method according to the invention.

Example 2

This example investigates the antioxidant capacity in phenolic-fortified chocolate compared to non-fortified chocolate.

Method

The antioxidant capacity of 6 pieces of control milk chocolate (1 piece from each row of an approximately 100 g block) and 12 pieces of phenolic-fortified milk chocolate (2 pieces from each row alternating $1^{st}$ and $3^{rd}$, $2^{nd}$ and $4^{th}$) were chosen for assay. The milk chocolate was provided by Cool Health Pty Ltd. A sample of each, weighing between 1.7 and 2 g, was weighed accurately and added to a 50 ml tube. The chocolate samples were defatted by the addition of 20 ml heptane. The samples were centrifuged and the heptane decanted. The samples were left open in a fume hood to remove traces of heptane. The antioxidants were extracted using 2×20 ml aliquots of 80% methanol, the first a 2 hour extraction and the second an overnight extraction. The primary and secondary extract were added together and assayed in duplicate using the ABTS method after a 5-fold dilution in water.

Results

TABLE 3

Antioxidant capacity in chocolate

| Control chocolate | | Fortified chocolate | |
|---|---|---|---|
| Sample (Row, Position) | Antioxidant Capacity (mg catechin equivs/g) | Sample (Row, Position) | Antioxidant Capacity (mg catechin equivs/g) |
| 1, 1 | 1.638 | 1, 2 | 1.832 |
| 2, 1 | 1.578 | 1, 4 | 1.857 |
| 3, 4 | 1.572 | 2, 1 | 2.022 |
| 4, 2 | 1.634 | 2, 3 | 1.859 |
| 5, 3 | 1.547 | 3, 4 | 1.924 |
| 6, 4 | 1.557 | 4, 1 | 1.914 |
| | | 4, 3 | 1.937 |
| | | 5, 2 | 1.971 |
| | | 5, 4 | 1.936 |
| | | 6, 1 | 2.016 |
| | | 6, 3 | 1.900 |

Discussion

The antioxidant capacity of the control chocolate was 1.587±0.039 mg catechin equivalents per gram (mean±standard deviation). The antioxidant capacity of the phenolic-fortified chocolate was 1.961±0.142 mg catechin equivalents per gram. This represents an increase of 21.2% compared with the control chocolate. It is thus possible for an effective amount of polyphenols to be added and uniformly distributed in a chocolate matrix to produce a formulation suitable for use in the methods according to the invention.

Example 3

This example investigated the polyphenol content of extracts of various sugar cane products at different stages in the sugar refining process. A catechin equivalent assessment of first expressed juice, final juice, syrup, molasses, low pol sugar, mill mud, cane tops and foam was undertaken.

Results

TABLE 4

Antioxidant potential of various sugar cane extracts

| | Total Antioxidant Potential (CE = catechin equivalents) | |
|---|---|---|
| Sample | (mg CE/mL) | (mg CE/g dry matter) |
| First Expressed Juice | 0.75 | 3.40 |
| Final Juice | 0.12 | 8.76 |
| Syrup extracted from the clarified juice | 2.89 | 3.43 |
| Molasses | 23.58 | 30.00 |
| Low pol Sugar | — | 2.34 |
| Filtrate | 0.44 | 3.64 |
| Cane tops | 0.44 | 13.54 |
| Foam | 0.23 | 3.75 |
| Mill Mud | — | 3.17 |
| Raw Sugar | 0.44 | — |

TABLE 5

Antioxidant potential of sugar cane extracts vs other polyphenol sources

| Sample | Polyphenols (mg catechin equivs/g) | Anti-oxidants (µmoles/g) |
| --- | --- | --- |
| Dark Chocolate | 23.9 | NT |
| Milk Chocolate | 7.25 | 18.3 |
| Cocoa liquor | 41.8 | 110 |
| Grape Seed Powder | 301.5 | 1146 |
| Grape Skin Extract | 54.5 | 181 |
| Mixed Berry Snack | 12.3 | 9.33 |
| Mixed Juice | 3.35 | NT |
| Mill mud | 14.7 | 26.8 |
| Molasses | 17.87 | 32.58 |
| Raw sugar | 0.25 | 0.44 |

The analysis revealed that the extracts from molasses and mill mud contain a significant amount of polyphenols and thus could be added to a formulation suitable for use in the methods according to the invention.

Example 4

Figure 1:
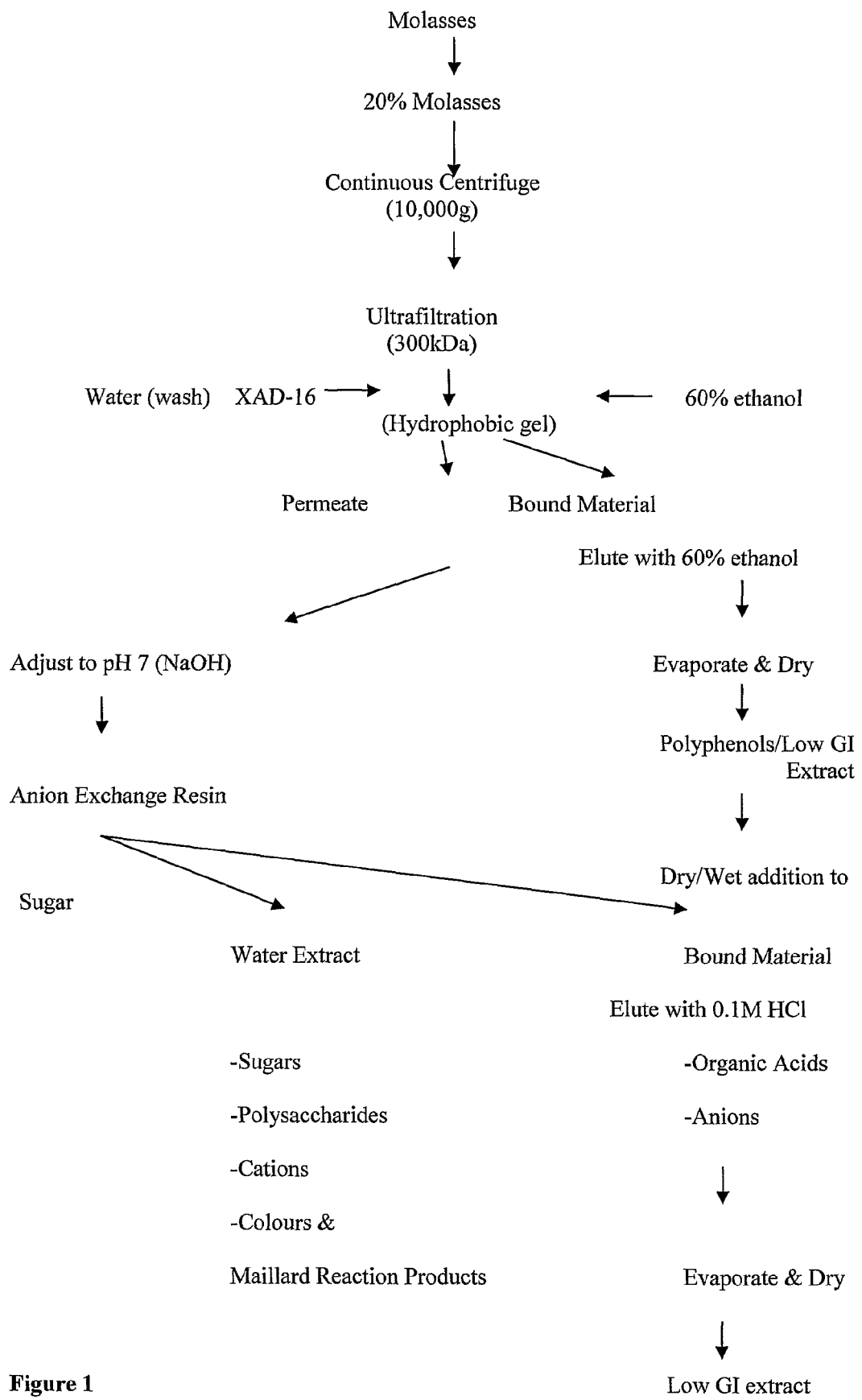
FIG. 1 shows the extraction method used in Example 4.

This example demonstrates the production of a sugar product containing polyphenols which can be used in a formulation for use in a method according to the invention. The flowchart in FIG. 1 illustrates the process used to produce a sugar cane molasses extract high in polyphenols. The extraction of sugar cane molasses is discussed in more detail in international patent application no 2005/117608.

A High Pol Sucrose base was prepared which comprised 99% total sucrose, glucose and fructose (wherein the amount of glucose and fructose was no more than 0.5%) and 1% of a mixture of organic acids, minerals, polyphenols, antioxidants and polysaccharaides. This mixture consisted of the following:

- 600 to 2100 micrograms per gram of a mixture of trans-aconitic acid, oxalic, cis-aconitic, citric, phosphoric, gluconic, malic, succinic, lactic, formic and acetic acids, wherein most of the mixture consisted of trans-acotinic acid in an amount in the range from 200 to 600 micrograms per gram;
- 150 to 600 micrograms per gram of minerals with the ratio of calcium to magnesium to potassium being 50:15:35;
- 0.2 to 0.5 mg catechin equivalents per gram of polyphenols;
- antioxidants so that the antioxidant activity is in the range of 0.4 to 1.2 micromoles per gram; and
- 20 to 60 micrograms per gram of polysaccharides.

A sweetener high in phenolics was prepared by combining the High Pol Sucrose base with the extract high in polyphenols obtained above.

Electrospray Mass Spectrometry (ES/MS) was conducted on a Micromass Platform ES/MS. The samples were dissolved in Methanol/Water (80:20) and injected into a 20 µl loop and eluted with methanol/water (80:20) at 20 µl/min. MS analysis was conducted in negative ion mode with a cone voltage of 40 kV and a mass range of 50-700 Da.

The sugar product contained a significant amount of polyphenols and thus could be added to a formulation suitable for use in the methods according to the invention.

Example 5

This example demonstrates the production of a commercial chocolate product containing polyphenols which can be used in the method according to the invention.

Infusion of Currants

Infusion Mixture: The following mixture (25 liters) was sufficient to infuse 125 kg of currants which is sufficient for 1000 kg of chocolate.

20 liters Wine eg Shiraz, Merlot or Pinot Noir)
5 liters Grape Skin/Seed Extract
125 ml Flavouring Mix the above well in a large vessel at room temperature Stir slowly to ensure that the grape skin/seed extract and flavour is well blended mixed with the wine.

The flavouring can be any natural or synthetic flavours depending upon the specific note and profile desired in the finished chocolate. The flavour may have an alcoholic, monosaccharide, polysaccharide, polydextrose, polydextrin, dextrin, polyol, starch, propylene glycol, vegetable oil, triglyceride or other suitable base/carrier.

A non-alcoholic infusion mix can also be utilised if required by substituting the wine variety by a non-alcoholic, de-alcoholised variety. In addition a range of non-alcoholic or de-alcoholised flavours can also be added to the infusion mix to improve taste and deliverability of the currants in the chocolate.

Infusing the Currants: Combine currants and infusion mixture in a vessel which can be rotated to fully mix the contents. Rotate the vessel regularly for the next 24 hours. Filter/strain off any excess liquid and spread the infused currants on a drying rack and place in a warm room (40° C.) with air flowing across the currants overnight.

Preparation of Chocolate Containing Grape Seed Powder and Flavouring

Base Chocolate Recipe (per 500 kg (0.5 t batch)):

| Ingredient | Amount |
| --- | --- |
| Castor Sugar | 200 kg |
| Full cream milk powder | 70 kg |
| Cocoa Liquor (Ivory Coast) | 175 kg |
| Cocoa Butter Deodorised | 50 kg |
| Soy Lecithin - (Add half initially and half 30-60 mins before finishing conching cycle) | 2.5 kg |
| PGPR - (Add half, 1 kg, initially and remainder after addition of flavours (to reduce viscosity).) | 2.0 kg |
| Natural Vanilla Flavour - (Add 30 mins before finishing conching cycle) | 2.0 kg |

Add to conche in correct sequence and conche for 12-16 hours at 40° C. until average particle size of chocolate reaches less than 20µ (range 18µ-20µ). The chocolate was then flavoured as one of shiraz, pinot or merlot. The chocolate has a milk fat to cocoa butter ratio of 0.13.

The real varietal wine flavour in the chocolate can be enhanced by adding a range of flavours that not only enhance the flavour but serve to reduce the bitterness when higher than usual amounts of polyphenols are added to promote health. A person skilled in the art of flavour chemistry will know which mix of flavours may be used to improve palatability, mouth feel and other organoleptic properties.

Preparation Of Seed Powder (for 0.5 tonne batch of chocolate): Weigh out 2.25 kg of Vinlife (Tarac Technologies) Grape Seed Powder and add to 5 kg of melted (45° C.) cocoa butter. Add slowly with stirring and ensure the powder is dispersed evenly throughout the cocoa butter. Avoid incorporation of air whilst mixing, but ensure that the powder is well dispersed in the cocoa butter.

Addition Of Seed Powder To Chocolate: To 0.5 tonne (500 kg) of wine-flavoured chocolate held in holding tank at 40-45° C. add the 5 kg of cocoa butter containing the dispersed seed powder. Add slowly and mix in the tank for 5 minutes or until evenly dispersed.

Addition of Infused Currants to Chocolate

The filtered and drained currants (approx 5.5-5.8 kg) were mixed with 40 kg of the flavoured and tempered chocolate. The mixture must be mixed well to ensure an even distribution of the currants.

The currant/chocolate mixture is then moulded and cooled.

By using dried currents or fruit infused with wine and water-soluble polyphenols dispersed in cocoa butter, difficulties typically experienced with addition to foods such as chocolate can be overcome. Taste can further be improved using wine flavours and a uniquely palatable product can be produced with enhanced polyphenol content, antioxidant and ACE inhibitory activity for use in the methods according to the invention.

Example 6

In this example, sugar polyphenols or molasses extract from example 4 were tested to determine the effect on body mass distribution of mice.

Method

In this experiment disease free six week old male C57B1/6J mice (n=65) were used. The mice were purchased from the Animal Resource Centre, Canning Vale, WA, Australia.

Several days after arrival in the animal house, mice were shifted from their normal chow diet (3% fat) to a high fat-high carbohydrate diet (21% fat, 20% protein, 49% carbohydrate, 5% cellulose, 5% vitamins and minerals). The diets were specially formulated by Specialty Feeds, Glen Forrest, Wash., Australia. All animals were housed 2 per group at 19-21° C. with a 12:12 light dark cycle.

Three groups of mice (n=13 mice per group) were maintained on the high fat-high carbohydrate diet containing (1) 1% polyphenol-containing powder; (2) 2% polyphenol-containing powder; (3) molasses; (4) 1% sucrose (control). The diets used in this example were made by combining 98-99% of the base diet plus 1-2% of the additives noted above. The animals were fed the diets for 9 weeks.

During the 9 week period, food and water intakes and body weight was measured weekly. At week 9 body composition of mice was determined using Dual Energy X-ray Absorptiometry (DEXA).

Dual Energy X-ray Absorptiometiy (DEXA): Whole body composition of mice was assessed using DEXA (Norland XR-36) equipped with software package optimized for small animals. The mice were scanned under light anaesthesia (Ketamil and Rompun). A whole body scanning mode was used providing information such as % body fat, bone mineral content (BMC), bone mineral density (BMD), and Lean mass. Animals were placed in the prone position at the centre and parallel to the long axis of the scan table.

Results and Discussion

Figure 2:
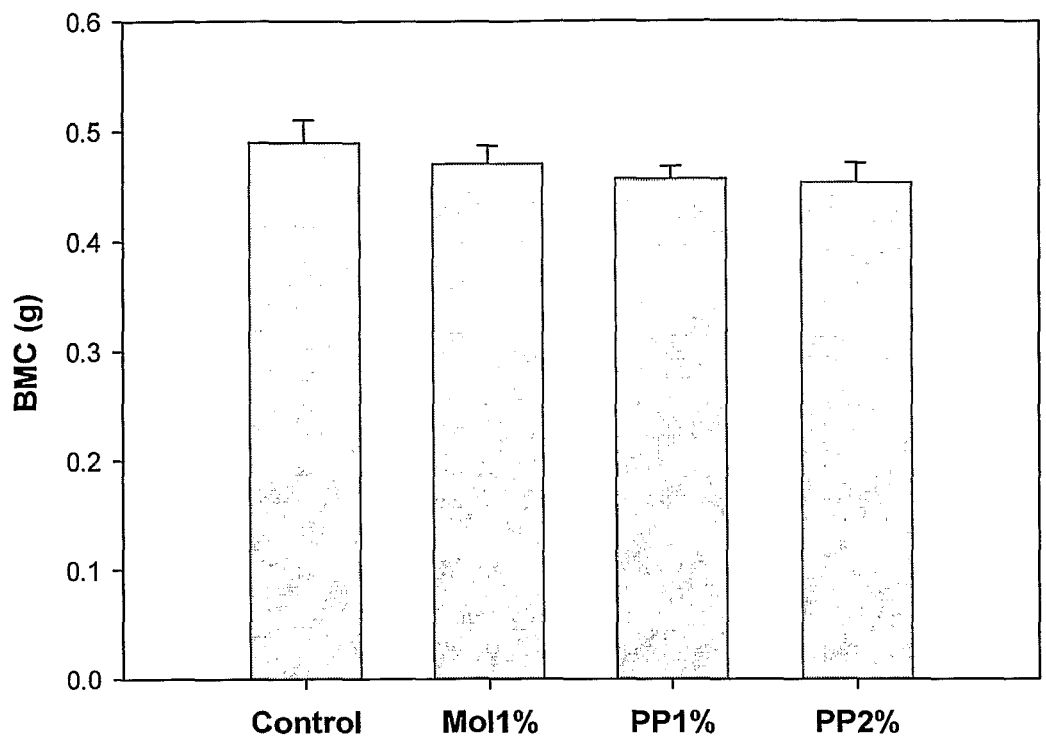
FIG. 2 shows the Bone Mineral Content results from Example 6.
Figure 3:
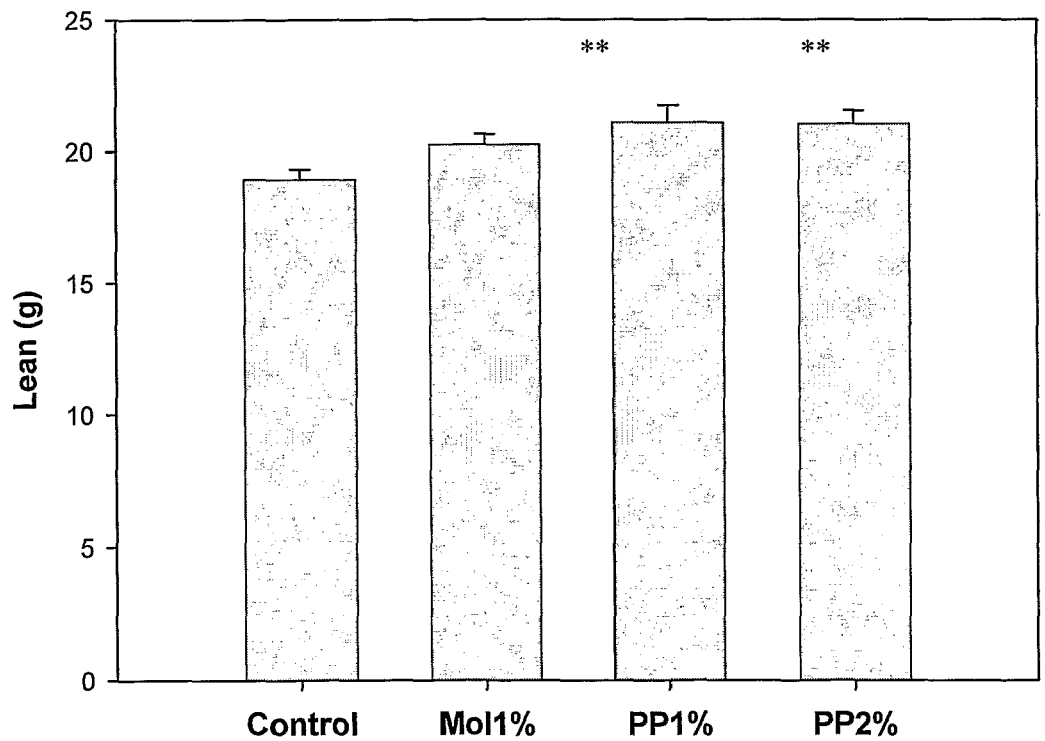
FIG. 3 shows the Lean Muscle Mass results from Example 6.
Figure 4:
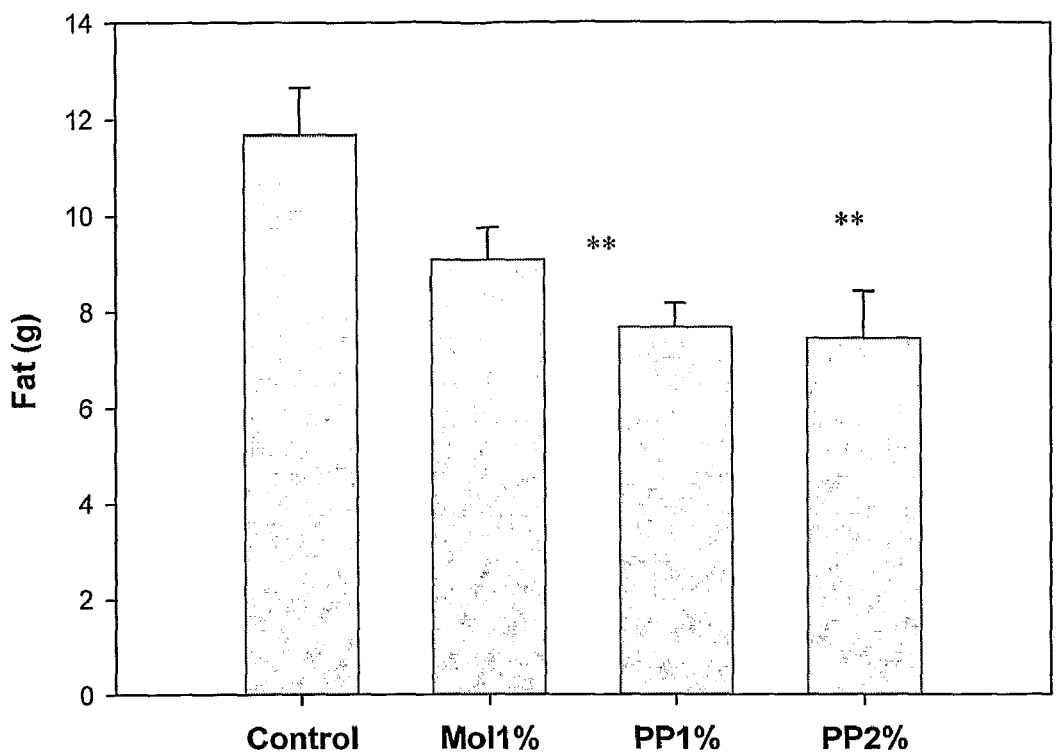
FIG. 4 shows the Fat Mass results from Example 6.
Figure 5:
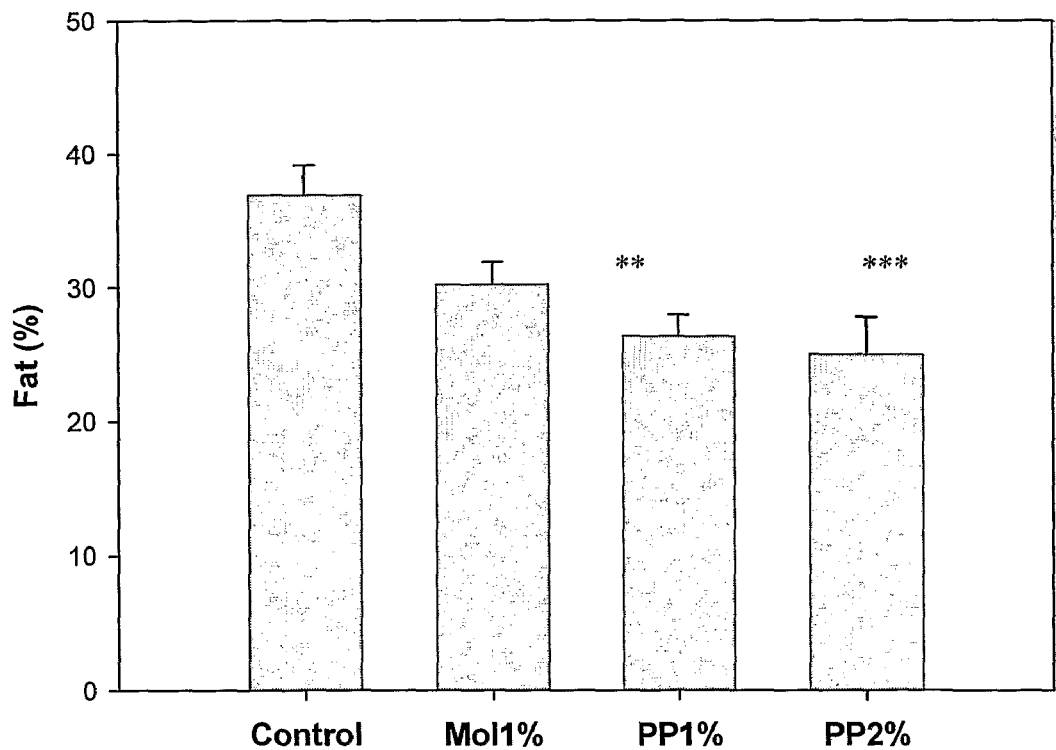
FIG. 5 shows the Percentage Fat results from Example 6.
Figure 6:
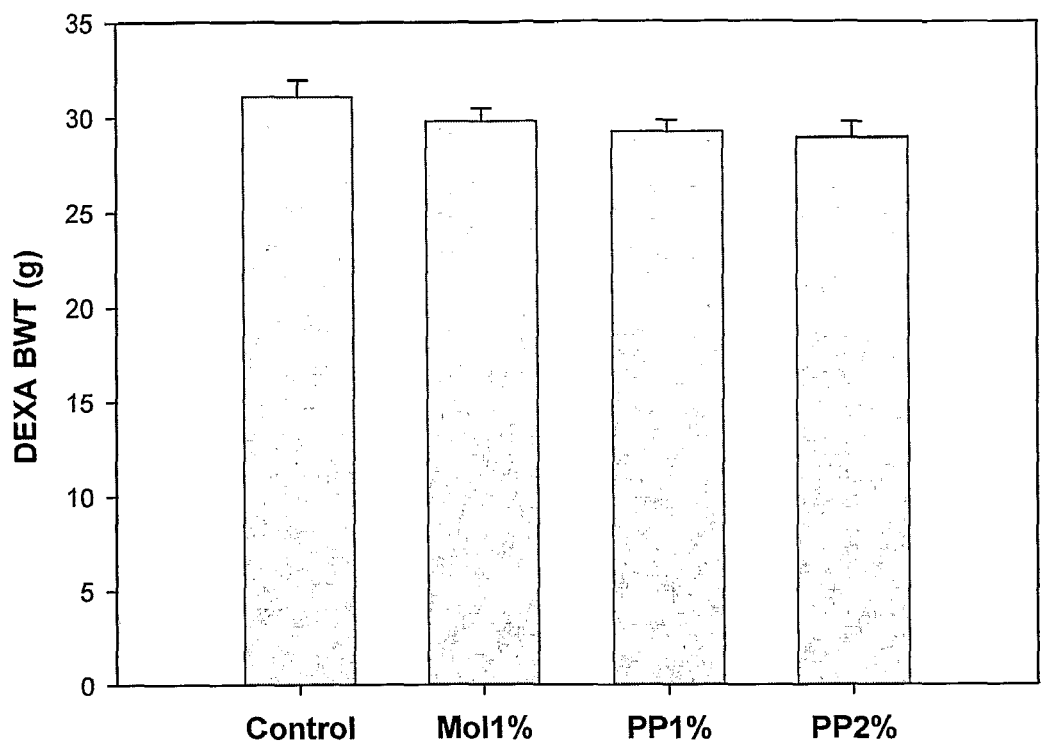
FIG. 6 shows the Total Body Weight by DEXA results from Example 6.
Figure 7:
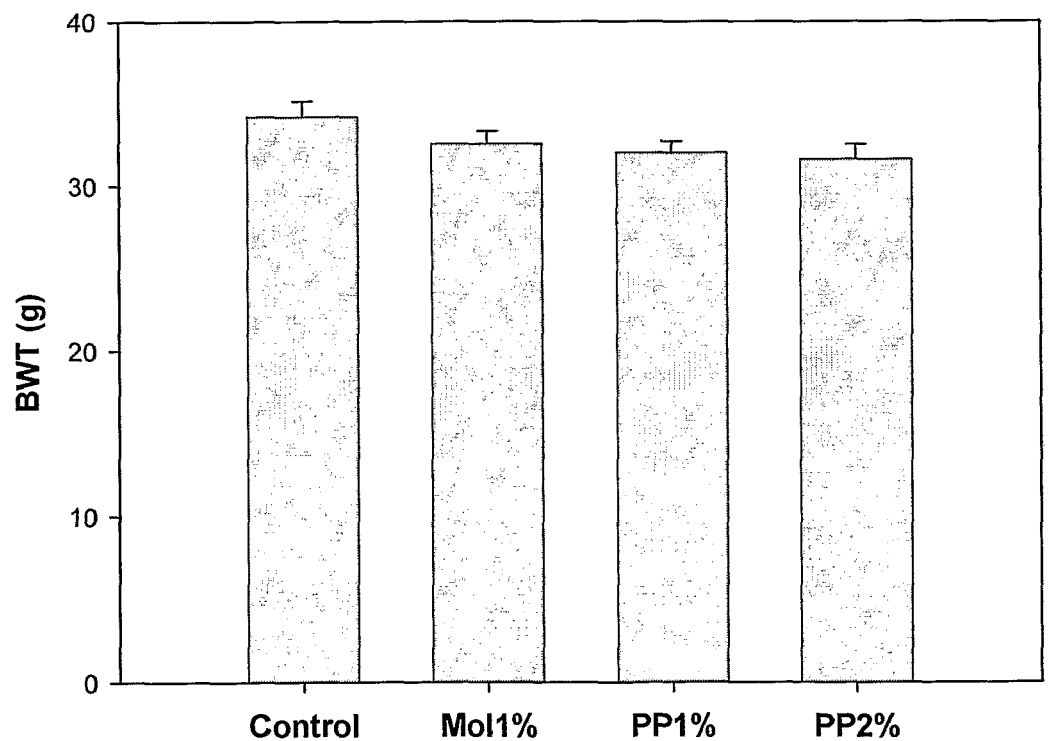
FIG. 7 shows the Total Body Weight results from Example 6.
Figure 8:
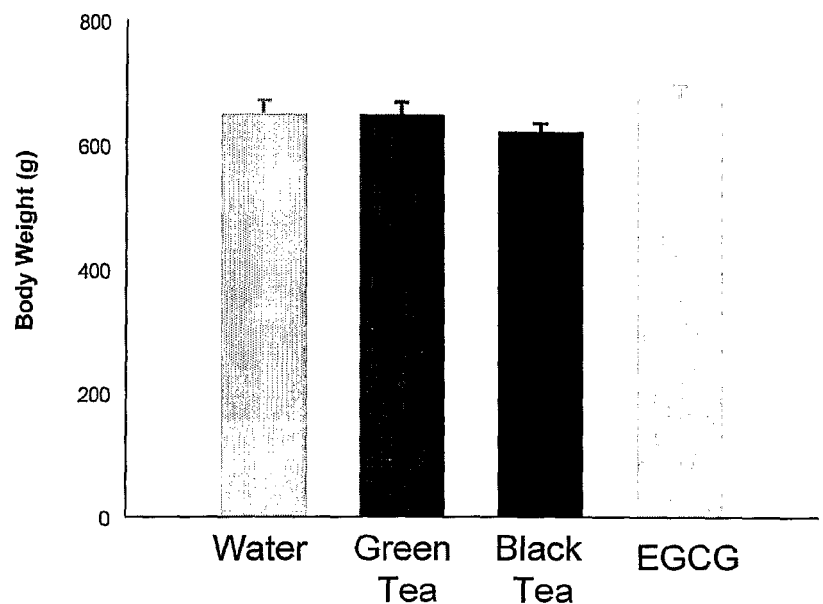
FIG. 8 shows the body weight at the time of glucose loading results for Example 8.
Figure 9:
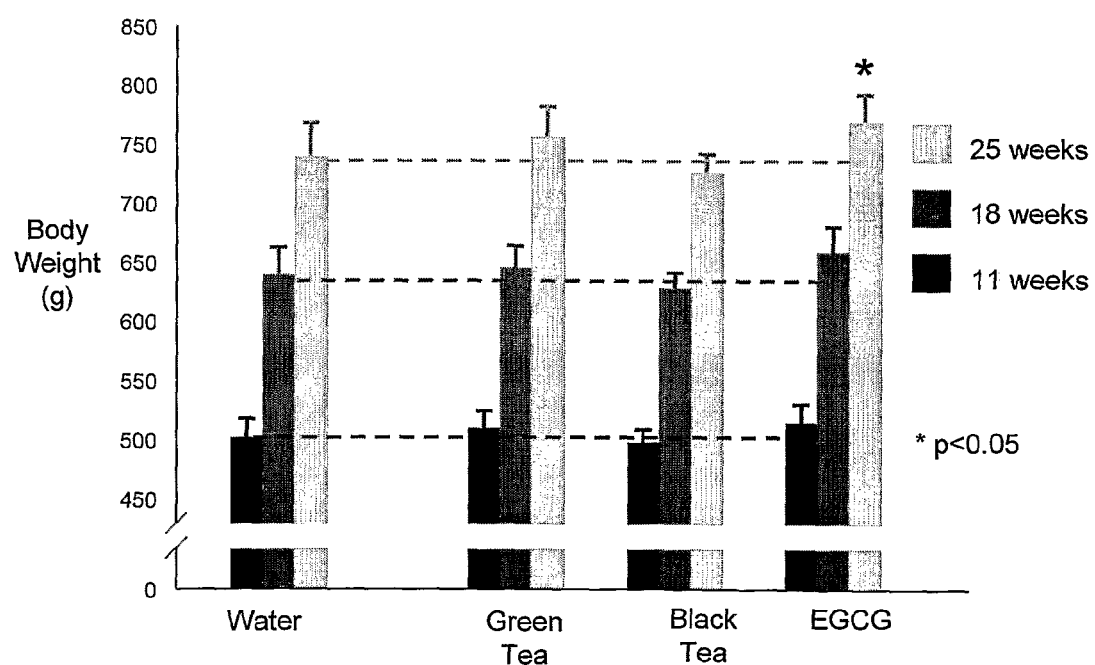
FIG. 9 shows the body weight at the time of DEXA analysis for Example 8.
Figure 10:
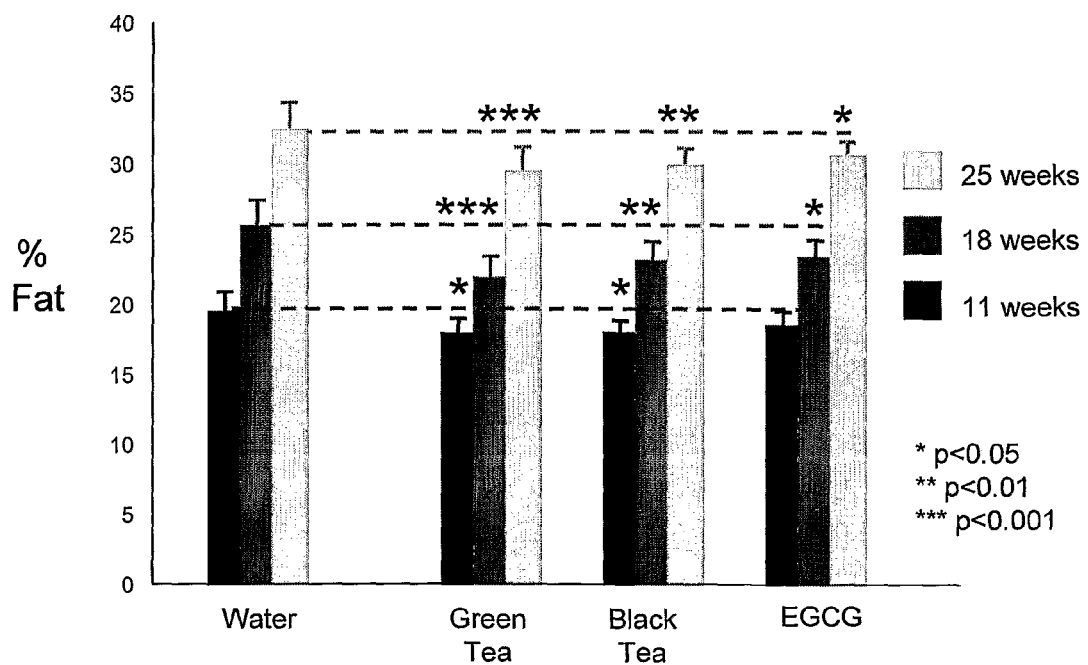
FIG. 10 shows the percentage of fat mass at the time of DEXA analysis for Example 8.
Figure 11:
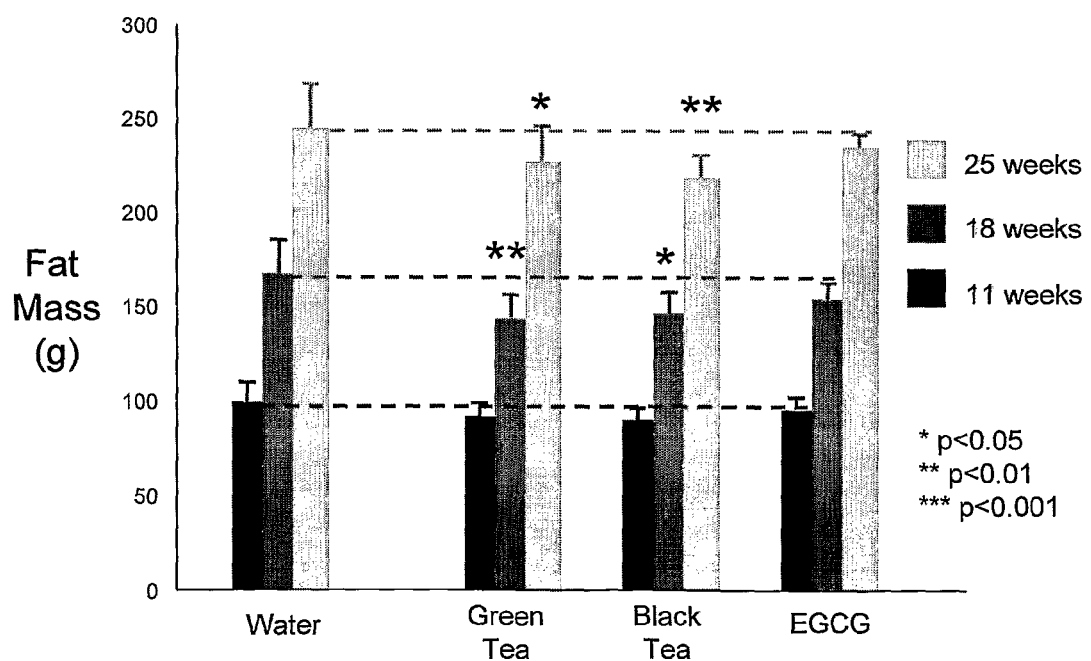
FIG. 11 shows the fat mass in grams at the time of DEXA analysis for Example 8.
Figure 12:
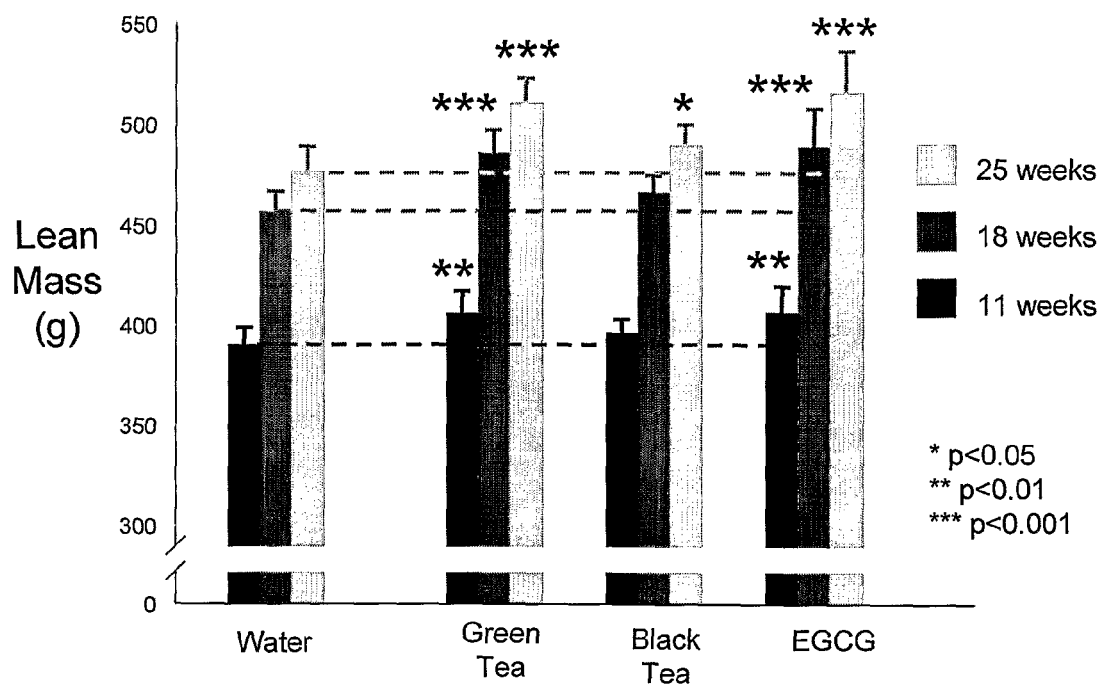
FIG. 12 shows the lean mass in grams at the time of DEXA analysis for Example 8.
Figure 13:
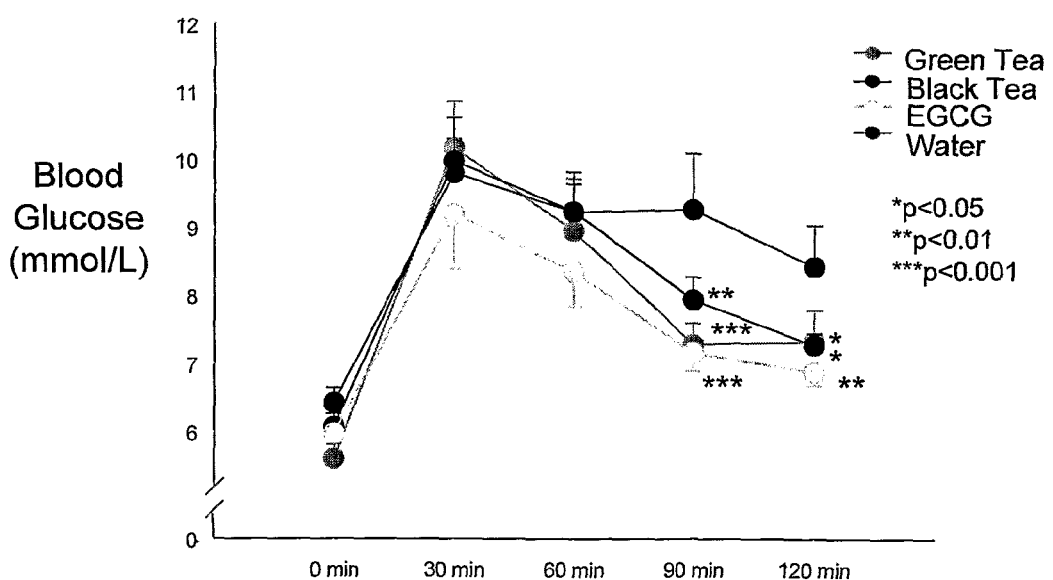
FIG. 13 shows the blood glucose results for Example 8.
Figure 14:
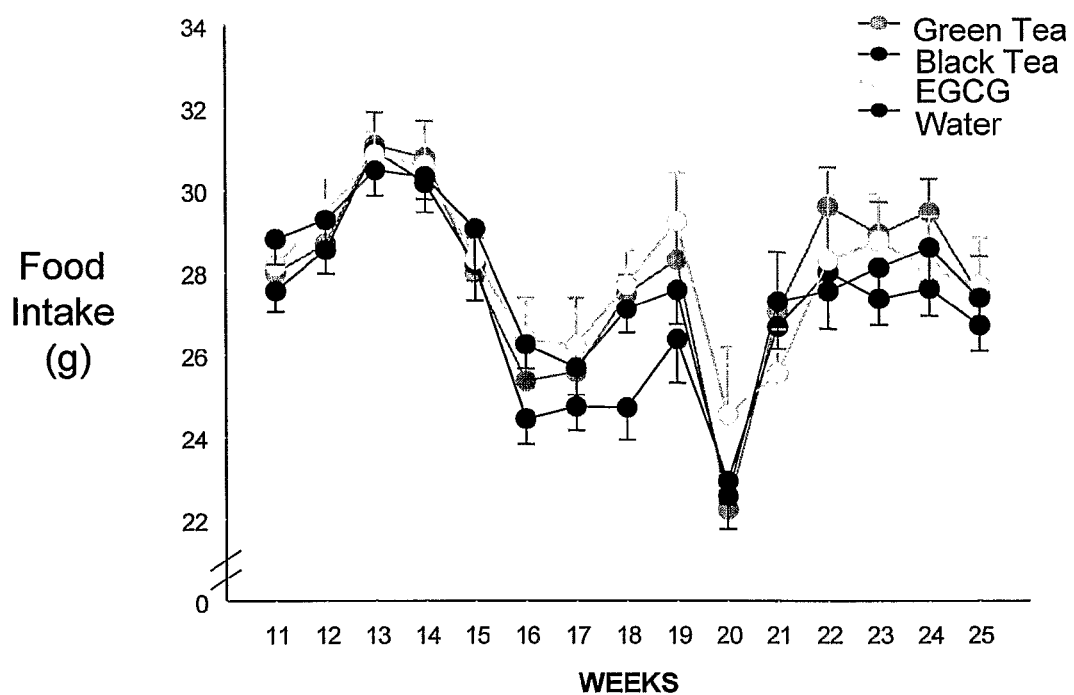
FIG. 14 shows the food intake results for Example 8.
Figure 15:
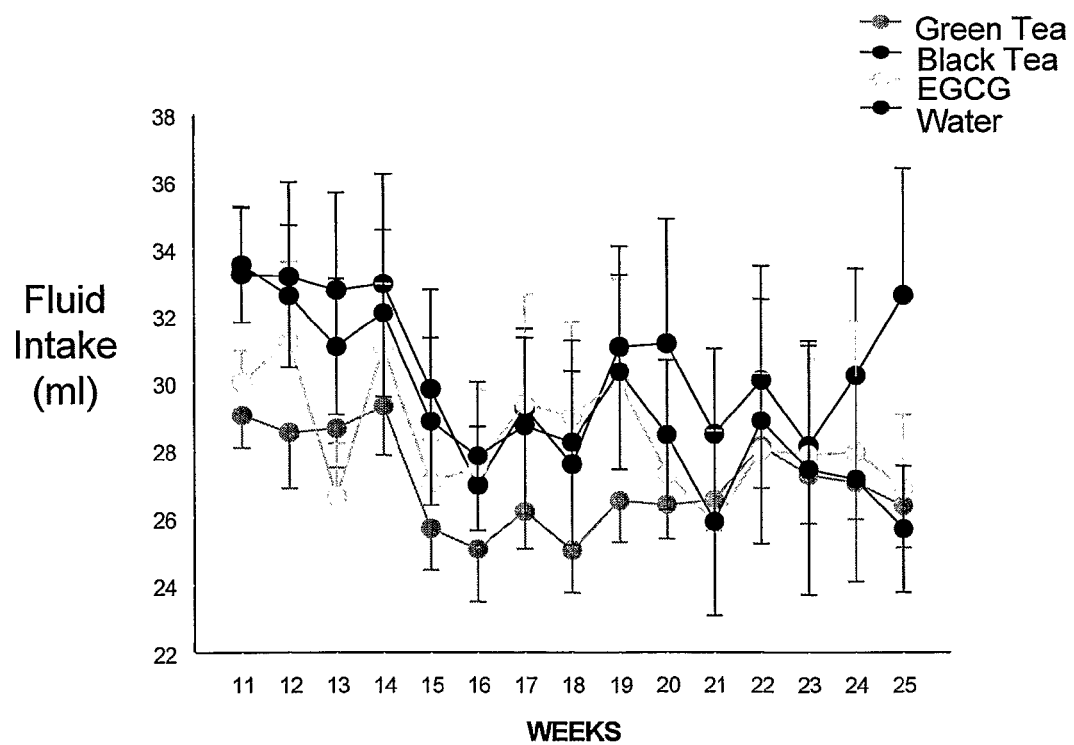
FIG. 15 shows the fluid intake results for Example 8.
Figure 16:
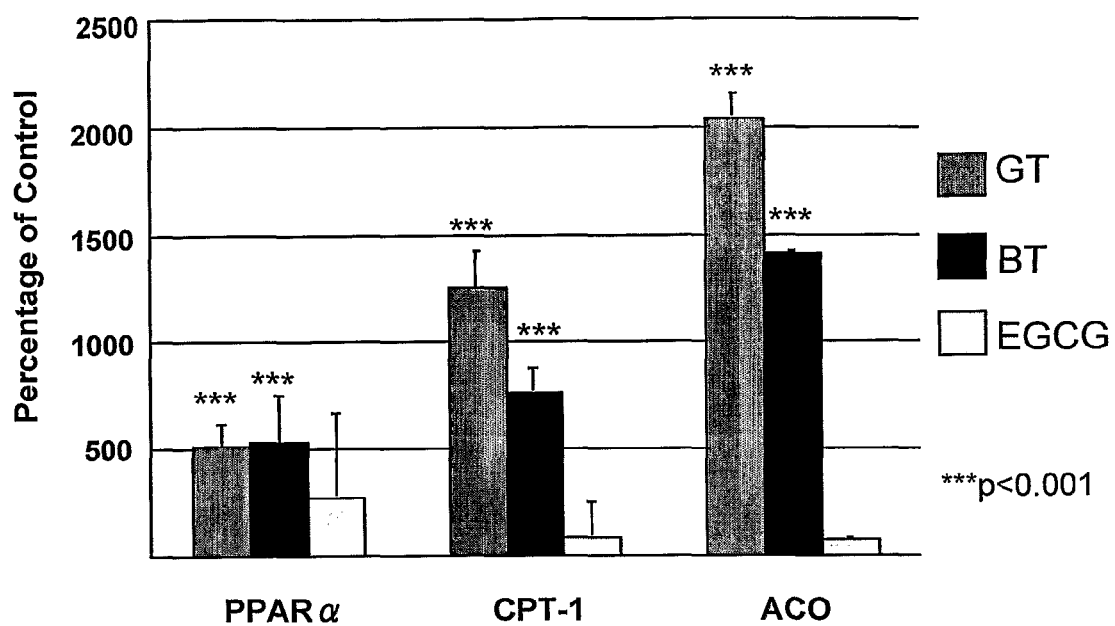
FIG. 16 shows the liver fat oxidation results for Example 8.

Polyphenol powder and molasses added to the high fat diet, at both 1 and 2% (PP1%, PP2%), decreased body fat (in grams—see FIG. 4 or as a % of body weight—see FIG. 5) and increased lean mass (see FIG. 3). Body weight and bone mineral content was not significantly altered (FIGS. 2 and 6). DEXA was undertaken after 9 weeks of dietary intervention. DEXA body weight (sum of lean, bone and fat) was highly correlated with body weight measured on a balance (r=0.98).

In FIGS. 2 to 7, statistical analysis by one way analysis of variance and subsequent Fisher LSD post hoc test; vs control, *$p<0.05$; $p<0.01$; *$p<0.001$.

There were no differences in food or water intake (not shown). The current figures do not show that molasses decreased body fat; i.e., Fat %, mean (SEM), control=36.9 (2.3), molasses=30.2 (1.7), PP1%=26.3 (1.6), PP2%=25.0 (2.8).

Conclusion

The results clearly demonstrate that the polyphenol powder changed body composition by significantly increasing lean muscle mass and significantly decreasing percentage fat. The mean reduction of 11.9% fat and 6% increase in lean muscle mass would significantly improve the prognosis for those suffering from obesity, diabetes and cachexia.

Example 7

In this example, the molasses extract of example 4 and which was used in example 6 was tested for antioxidant capacity (ORAC) and influence on the activity of α-glucosidase and α-amylase.

Materials and Methods

Sample Preparation: Samples were ground and approximately 50 mg was solubilized in 5 mL of methanol. The samples were vortexed, sonicated for 30 minutes, and centrifuged for 5 minutes (1900 RCF). The supernatant was collected and taken to dryness. Samples were re-solubilized in methanol at 10 mg/ml.

Molasses powder samples were directly water-soluble. Molasses powder was solubilized in phosphate buffer (pH 7.4) at a concentration of 1 mg/ml, prior to the ORAC assay. The molasses powder sample was also extracted as above, to provide comparative ORAC data. Molasses powder was solubilized in water prior to the a-amylase and a-glucosidase assays.

Oxygen Radical Absorbance Capacity (ORAC) assay: The ORAC assay employed in this study measured the antioxidant scavenging activity in the test sample, against peroxyl radicals induced by 2,2'-azobis (2-amidinopropane) dihydrochloride (AAPH) at 37° C. Fluorescein was used as the fluorescent probe. Hydrophilic ORAC values were determined for the samples.

The extracts/samples were assayed using the ORAC procedure in serial dilution (×4) with AWA (acetone: water: acetic acid; 70:29.5:0.5), and in quadruplicate, starting with the concentration relevant to the sample, depending on the approximated antioxidant capacity from an initial screen. A green tea extract was included as a positive control, and the extract was prepared as per the sample preparation.

Molasses powder sample was directly solubilized in phosphate buffer (pH 7.4), and assayed, with the exception of AWA being substituted with phosphate buffer (pH 7.4). A methanolic green tea extract was included as a positive control, and was also solubilized in phosphate buffer (pH 7.4).

Trolox, a water soluble analogue of vitamin E, was used as a reference standard. A trolox standard curve was established from trolox standards prepared at 100, 50, 25, and 12.5 μM in AWA.

Briefly, 20 μL samples/standards/control/blank (AWA), 10 μL fluorescein ($6.0\times10^{-7}$ M), and 170 μL AAPH (20 mM) were added to each well. Immediately after loading, the plate was transferred to the plate reader preset to 37° C., and the fluorescence was measured 35 times at one minute intervals. The fluorescence readings were referenced to solvent blank wells. The final ORAC values were calculated using a regression equation between the Trolox concentration and the net area under the fluorescein decay curve, and were expressed as micromole Trolox equivalents (TE) per g of sample.

Glucose Metabolism Enzyme Inhibition Assays

α-Glucosidase: Molasses powder sample was solubilized in water prior to use in this assay. Fucoidan was included as a positive control, and was also solubilized in water.

Glucosidase enzyme was solubilized in acetate buffer (50 mM, pH 4.5) at a concentration of 0.7 mg/mL. This provided a final concentration of 0.2 U/mL. To a 96-well plate, 50 μL of enzyme was added to each well. A corresponding set of wells was also included, in which acetate buffer was added instead of enzyme. Sample/controls were then added to the wells (5 μL), in triplicate, followed by the substrate 4-Nitrophenyl-α-D-glucopyranoside (final concentration 2 mM). The plate was covered, shaken and then incubated at 37° C. for 30 minutes. The reaction was stopped with the addition of 0.2 M $Na_2CO_3$ (100 μL/well). Absorbance was measured at 405 nm, using a Victor$^2$ plate reader.

The absorbance of the wells containing sample, substrate, and buffer were subtracted from the corresponding wells containing the glucosidase enzyme and the percent inhibition by the samples was calculated compared to the solvent controls.

α-Amylase: Molasses powder sample was solubilized in water. Acarbose was included as a positive control. Acarbose tablets were crushed and solubilized in 50% aqueous ethanol (56 mg/mL). The solution was sonicated and centrifuged at 2000 RCF for 10 minutes. The supernatant was collected and stored at 4° C.

An Enzchek Ultra Amylase assay kit was used to determine the influence of sample 1 on α-amylase activity (Molecular Probes E33651). Briefly, a 1× reaction buffer (supplied with the kit) was prepared by diluting the stock 1:10 with distilled water. One vial of lyophilised starch substrate (DQ™ starch from corn, BODIPY® FL conjugate) was prepared by adding 100 μL of 50 mM sodium acetate (pH 4.0) and then 900 μL of 1× reaction buffer, followed by 20-fold dilution with 1× reaction buffer. An amylase stock solution was prepared by solubilising 0.5 mg/mL of porcine α-Amylase (Sigma A3176) in distilled water. The amylase stock was then diluted with 1× reaction buffer to provide a concentration of 125 U/ml.

The assay was performed using a 96-well plate format. 100 μL of amylase enzyme solution was added to each well, followed by the samples and controls (5 μL/well). The substrate solution was then added (95 μL/well) and the fluorescence (excitation at 485 nm, emission at 530 nm) was measured using a Victor plate reader.

Results and Discussion

The yield from each product is presented in Table 6.

TABLE 6

Yield of extract from each sample

| Sample | Sample mass (mg) | Extract mass (mg) | Yield (%) |
|---|---|---|---|
| Molasses Powder | 49.8 | 34.3 | 69 |
| Green tea | 48.5 | 16.3 | 34 |

Antioxidant Capacity: The antioxidant capacities of the samples, prepared by making methanolic extracts, are presented in Table 7. The molasses powder sample demonstrated the greatest antioxidant capacity, with an ORAC value of 4395 μmol TE/of sample when an extract was generated or 5020 μmol TE/of sample when dissolved directly in buffer (Table 8). Both values were considerably higher than the corresponding green tea extract.

TABLE 7

Antioxidant capacity of molasses powder extracted with methanol, compared to a green tea methanol extract (values are mean ± standard error of the mean).

| Sample no. | ORAC value (μmol TE/g of sample) |
|---|---|
| Molasses Powder | 4395 ± 229 |
| Green tea | 1793 ± 93.5 |

TABLE 8

Antioxidant capacity of molasses powder solubilized directly in phosphate buffer (pH 7.4), compared to a green tea methanol extract (values are mean ± standard error of the mean)

| Sample no. | ORAC value (μmol TE/g of sample) |
|---|---|
| Molasses Powder | 5020 ± 375 |
| Green tea | 1467 ± 90 |

Glucose Metabolism Enzyme Inhibition Assays

Inhibition of α-Glucosidase: Molasses powder sample 1 inhibited α-glucosidase to a limited extent, compared to the facoidan control (Table 9). The data from this assay was problematic, as the molasses powder sample exhibited a high background absorbance, which was subtracted from the corresponding wells containing the glucosidase enzyme. This possibly has caused an over-estimation of the inhibition in α-glucosidase activity, as inhibition is calculated compared to the solvent control, which had a relatively low background absorbance.

TABLE 9

Inhibition (%) of α-glucosidase by sample 1, compared to fucoidan (values are mean ± SEM)

| Sample | Concentration (μg/mL) | % Inhibition | $IC_{50}$ |
|---|---|---|---|
| Molasses Powder | 600 | 88.9 ± 0.7 | 194 μg/mL |
| | 300 | 65.7 ± 0.1 | |
| | 150 | 38.4 ± 0.5 | |
| | 75 | 12.9 ± 0.9 | |
| | 37.5 | 1.5 ± 0.2 | |
| | 18.7 | −3.8 ± 0.5 | |
| Fucoidan | 37.5 | 97.4 ± 5.9 | 14 μg/mL |
| | 18.8 | 73.5 ± 7.5 | |
| | 9.4 | 19.3 ± 2.7 | |
| | 4.7 | 5.7 ± 3.1 | |

Inhibition of α-Amylase

Sample 1 did not inhibit α-amylase activity, compared to the control, acarbose (Table 10). An $IC_{50}$ was not able to be calculated from this data because Sample 1 did not inhibit α-amylase activity sufficiently. An $IC_{50}$ could possibly be calculated should the sample be tested at much higher concentrations, but the biological relevance of such a concentration is questionable.

TABLE 10

Inhibition (%) of α-amylase by sample 1 compared to acarbose (values are mean ± SEM)

| Sample | Concentration (μg/mL) | % Inhibition | $IC_{50}$ |
|---|---|---|---|
| Sample 1 | 1200 | 9.5 ± 1.7 | — |
| | 600 | −3.6 ± 0.9 | |
| | 300 | −22.6 ± 1.6 | |
| | 150 | −30.4 ± 1.6 | |

TABLE 10-continued

Inhibition (%) of α-amylase by sample 1 compared to acarbose (values are mean ± SEM)

| Sample | Concentration (μg/mL) | % Inhibition | $IC_{50}$ |
|---|---|---|---|
| Acarbose | 1000 | 95.2 ± 30.1 | 147 μg/mL |
|  | 500 | 80.8 ± 10.2 |  |
|  | 250 | 61.5 ± 10.3 |  |
|  | 125 | 46.4 ± 9.1 |  |

Conclusion

This example clearly supports examples 1 and 4 by demonstrating by another method for measuring antioxidant capacity that the molasses extract is a potent antioxidant. The relative potency of molasses powder is as follows;
   grape seed extract>grape extract>molasses powder>green tea Products such as green tea, HCA (hyroxycitric acid), and inulin claim weight loss benefits based on the hypothesis that consumption of these products will delay glucose absorption and/or regulate insulin to control appetite. Glucose absorption is controlled by glucosidase and amylase. Molasses extract has weak glucosidase activity therefore it appears that the changes in body composition must be by other mechanisms of action. It is more likely that the mechanism involves inhibition of ACE.

Example 8

This example investigates the effect of polyphenols extracted from tea on body mass distribution.

Method

Animals and treatments: Male Sprague Dawley rats (n=48) were purchased from the Animal Resource Centre (Canning Vale, Wash.) at 3 weeks of age. Animals were allowed to acclimate for 1 week on Purina rat chow and water. From 4 weeks of age, all animals were provided with a semi-synthetic, high fat diet (15% fat, Table 6) (Specialty Feeds, Glen Forrest, Wash.) and administered one of four fluid treatments: Green Tea, Black Tea, Epigallocatechin Gallate (EGCG) or water. Tea and tea extracts were given as 100% of their fluid intake. Rats were maintained on the high fat diet and tea treatment until week 29. Food and fluid intakes were measured daily and body weights recorded weekly.

TABLE 11

Composition of high fat diet.

| Ingredient | % Composition |
|---|---|
| Sucrose | 10.93 |
| Casein | 20.00 |
| Soya Oil | 1.86 |
| Cocoa Butter | 2.51 |
| Ghee (Butter Fat) | 5.31 |
| Tuna Oil | 0.20 |
| Olive Oil | 4.23 |
| Flaxseed Oil | 0.91 |
| Cellulose | 5.00 |
| Starch | 31.5 |
| Dextrinised Starch | 13.2 |
| dl Methionine | 0.30 |
| AIN_93_G_Trace Minerals | 0.14 |
| Lime (Fine Calcium Carbonate) | 1.31 |
| Salt (Fine Sodium Chloride) | 0.26 |
| Potassium Dihydrogen Phosphate | 0.69 |
| Potassium Sulphate | 0.16 |
| Potassium Citrate | 0.25 |
| AIN_93_G_Vitamins | 1.00 |
| Choline Chloride 50% w/w | 0.25 |

Green and Black tea: Green and Black tea bags (Dilmah natural green tea™ and Dilmah black tea™) were purchased from a local retail outlet. Ten tea bags (approximately 2 g tea leaves/bag) were steeped in 1 liter of boiling tap water in a covered container for 3 minutes. Tea bags were then expelled of excess tea and the tea preparations made up to a 2 liter volume with cold tap water. This approximated to 1 tea bag per 200 ml of water. Tea preparations were made fresh every second day.

Epigallocatechin Gallate: Epigallocatechin Gallate (EGCG (98%), Sapphire Bioscience, VIC) was dissolved in the drinking water and administered at a dose of 1 mg/kg/day. EGCG preparations were made fresh daily.

Glucose Tolerance Testing: Animals were fasted overnight with ad libitum access to fluid. The following morning, rats were restrained and tails were immersed in local anaesthetic (Xylocaine) for 1 minute. A small segment was cut from the tip of the tail, and the tail massaged from the base to the tip until a small amount of blood appeared. Blood samples were collected (hemocue microcuvettes) and fasted basal blood glucose samples were taken (Hemocue Glucostat blood glucose analyser). An oral glucose load (40% glucose, bolus, 2 g/kg body weight) was then delivered by gavage and blood glucose measured at 30-minute intervals for 2 hours.

Dual Energy X-ray Absorptiometry (DEXA): Body composition was determined by dual energy x-ray absorptiometry using a Hologic QDR-4000/W Absorptiometer. Animals were lightly anaesthetised (Nembutal, I.P., 40 mg/kg) and placed supine on the scanning platform. Tails were taped in place and a whole body scan was taken. Fat, lean and total mass was measured, along with the percentage fat ratio and bone mineral content. Total mass as measured by DEXA was highly correlated with mass measured by weighing the animal (r=0.99).

Statistical analysis: Results from the glucose tolerance testing were compared using two-way analysis of variance (repeated measures) and a one way analysis of variance was used to compare DEXA and plasma insulin results. Both analyses were followed by the LSD test. Significance was reached when $p<0.05$. All results are presented as mean±SEM.

Results & Discussion

FIGS. 8 to 16 show the results obtained.

No change in blood glucose levels were observed as a result of the intervention.

The body weight for rats on all treatments was similar. The polyphenols did not alter the overall body weight.

At 11 and 18 weeks, the percentage of fat mass for the green tea and black tea treatments was significantly lower than that for the water control. At 18 weeks, the percentage of fat mass result for EGCG was also significantly different. At 18 weeks, the grams of fat mass was significantly lower than that for the water control. The polyphenols caused less fat mass to be produced when on the same food diet as the water control.

At 11 and 18 weeks, the grams of lean mass for the green tea and EGCG treatments was significantly higher than that for the water control. The polyphenols caused increased lean mass to be produced. The difference in the polyphenol content between green tea and black tea is likely to be the reason for the fact that black tea did not significantly alter the lean mass when compared to the water control.

Example 9

In this example, evaluation of angiotensin converting enzyme knock-out (ACE −/−) mice was undertaken to determine if they develop a phenotype of reduced fat mass.

Materials & Methods

Mice: Male and female heterozygous ACE knockout mice (+/−) were obtained from the laboratory of Pierre Meneton, Insern, U367, Paris, France. They were maintained on a C57BL/6J background in the animal house. Heterozygous (ACE +/−) mice were bred to produce wild type (ACE +/+) and homozygous ACE null offspring (ACE −/−). Real time polymerase chain reaction incorporating dual labelled-Taqman® probe technology (Applied Biosystems, Foster City, Calif.) was used for genotyping of ACE (−/−) and ACE (+/+) offspring. Mice were housed in individual plastic cages with sloping grill lids (Wiretainers, Melbourne, Australia). Food (Barastoc, Mouse Breeder cubes, Barastoc Stockfeeds, Australia) was available ad libitum on the sloping section of the lid and there was free access to tap water. The mice were maintained on a 12 hour light/dark cycle. Age matched male ACE (+/+) and ACE (−/−) mice pairs that were 12 months old and had been maintained in the same housing conditions were selected for the study. The amount of food and water consumed was monitored daily for one week.

In vivo visualisation of distribution of adipose tissue by Magnetic Resonance Imaging (MRI) Technique: Regional body fat distribution was visualised by magnetic resonance imaging (MRI). Images were acquired on a Bruker BIOSPEC 47/30 scanner, equipped with a horizontal 4.7 T Oxford magnet. Proton density weighted axial images with the following parameters:number of slices, 20; slice thickness, 1 mm; field of view (FOV) 6 cm; matrix, 256×256; repetition time (TR), 815 ms; echo time (TE), 17.9 ms were acquired. Mice were anaesthetised by placing them in an induction chamber with an exposure to an Isoflurane (Abbott Australiasia Pty Ltd, Sydney, Australia) concentration of 5% v/v in medical grade air and subsequent reduction to a concentration of 2%.

Body Composition Analysis by Dual Energy X-ray Absorptiometry (DEXA): The evaluation of the whole body composition of ACE (−/−) and ACE (+/+) mice were performed using DEXA (Hologic QDR 4500, Hologic Inc. USA) equipped with software package (version 3.07) optimized for small animals. The animals were scanned while in a prone position under light anaesthesia (0.02 ml/g body weight) with a mixture of ketamine (0.75 ml of 100 mg/ml Ketaplex, Apex Lab.) and xylazine (0.25 ml of 20 mg/ml Rompun, Bayer).

Blood Analyses: At the end of experiment, mice were sacrificed by bleeding from heart under anaesthesia by intraperitoneal injection of a Ketamine and Xylazine mixture described above. Blood was collected with heparin coated syringes and hematocrit was measured immediately after aspiration of a sample to a capillary tube followed by centrifugation in a micro centrifuge (HERMLE Z 233 M-2, Medos Company Pty Ltd, Victoria, Australia.) for 5 minutes at 10,000 rpm. Subsequently, the plasma was separated by centrifugation at 3,000 rpm for 15 minutes in a refrigerated centrifuge (Sorval-RT7) and stored at −80 degrees celcius until the biochemical analysis were completed. The plasma triglycerides, total cholesterol and glucose levels were measured by spectrophotometry according to the procedures described in commercially available kits (Beckman-Coulter Inc., Fulerton, Calif., USA). In ACE (−/−) and ACE (+/+) mice (n=6), plasma leptin was measured as previously described.

Measurement of Core Body Temperature (rectal temperature): Temperature was measured by K-type thermocouples connected to a dual channel Fluke 52 (John Fluke Manufacturing) electronic thermometer. To measure the rectal temperature, a thermocouple (coated in silicon at the tip) was inserted 2 cm into the anal sphincter of each mouse. The tip of the thermocouple and connecting wires were coated with 5% w/v lidocaine gel (Xylocaine, Astra Pharmaceuticals) as a local anaesthetic and lubricant. The temperature measurements were taken at the same time on four consecutive days and the average was taken of those four measurements.

Spontaneous Physical Activity on Running Wheel: Animals were allowed for 14 days ad libitum access to running wheels equipped with a speedometer (Sigma Sport BC 700 calibrated for running wheel radius) fitted to the individual plastic cage with grill lid. The distance run (km) and speed (km/h) were measured daily over 10 days. The mice were allowed free access to food and water.

Analysisfor Faecal Fat Content: Faeces were collected from mice cages over the period of one week and kept in the freezer (−20 degrees Celsius) until analysis. Lipids were extracted from 5 g of faeces using a 2:1 chloroform:methanol solution. The total lipid content was determined gravimetrically after extraction for 24 hours at room temperature. The dry weight of the faeces was determined on the lipid extracted residue. The total dry weight of the faeces was determined by adding the weight of fat content to the dry weight of faecal residue.

Statistical Analysis: All data is reported as mean+/−SEM. The differences between the two groups were analysed by a student t-test (Statistica, Statsoft, USA).

Results

TABLE 12

Plasma composition and hematocrit of ACE+/+ and ACE−/− mice

| Parameter | ACE+/+ | ACE−/− |
|---|---|---|
| Triglyceride (mmol/l, n = 7) | 0.85 ± 0.26 | 0.47 ± 0.06 |
| Cholesterol (mmol/l, n = 7) | 1.68 ± 0.14 | 1.97 ± 0.11 |
| Glucose (mmol/l, n = 7) | 14.31 ± 1.72 | 10.81 ± 0.87 |
| Hematocrit (%, n = 5) | 40.5 ± 0.9 | 27.5 ± 1.1*** |

The values are expressed as mean ± SEM;
***$p < 0.001$ (ACE−/− vs. ACE+/+)

Figure 17:
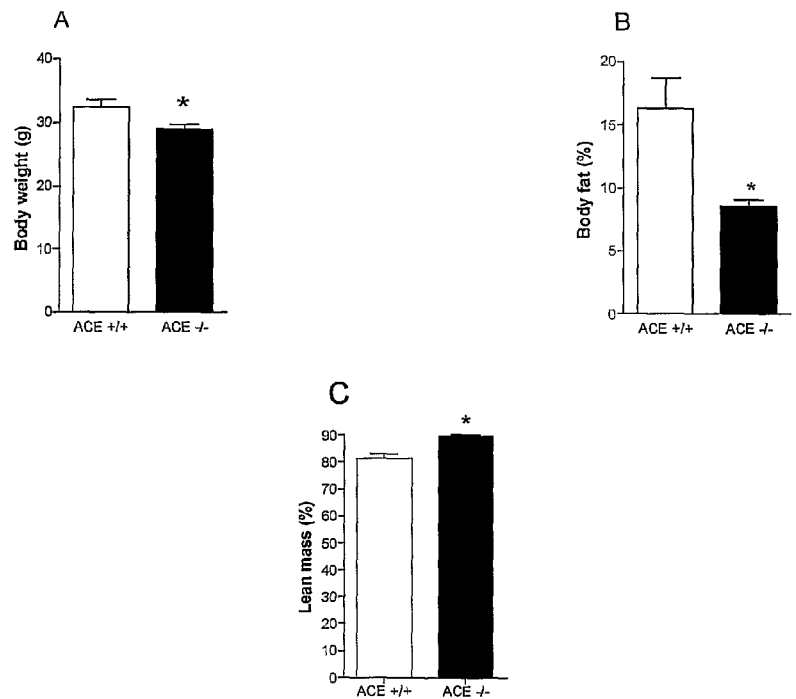
FIG. 17 shows the body weight (A), proportion of body fat (B) and proportion of lean mass (C) in ACE +/+ (empty bars) and ACE −/− mice (filled bars). The values are mean±SEM (n=7 per group), *p<0.05; p<0.01; *p<0.001.

Body Weight, Body Fat, Food and Water Intakes: In comparison to ACE (+/+) mice, the ACE (−/−) mice weighed 14-16% less ($p<0.01$); (FIG. 17A) and had 50-55% less body fat ($p<0.001$; FIG. 17B). ACE (−/−) mice had a significantly increased proportion of lean body mass compared with ACE (+/+) mice (FIG. 17C).

Figure 18:
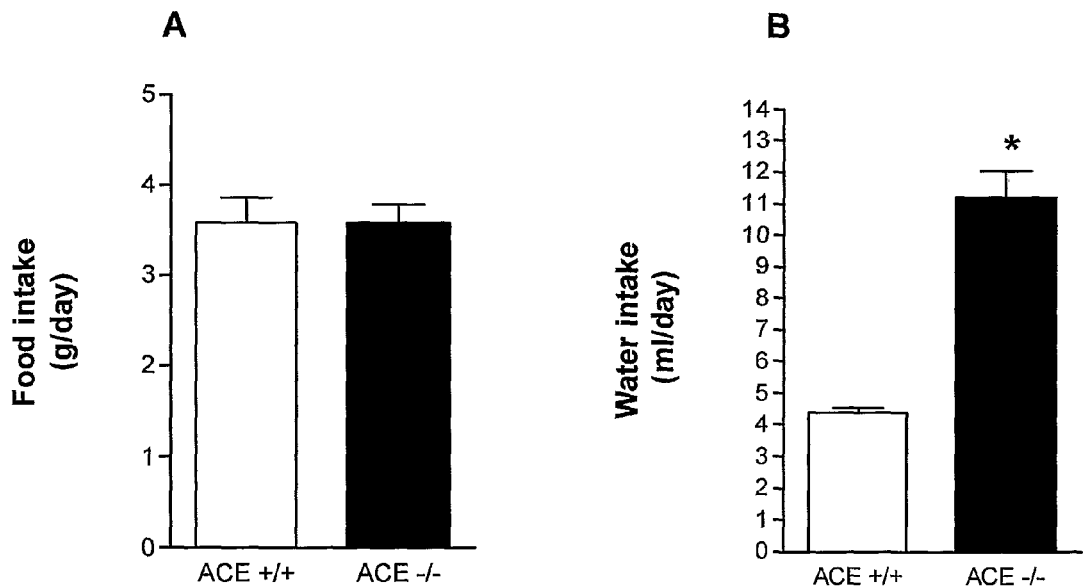
FIG. 18 shows the food (A) and water intake (B) in ACE +/+ (empty bars) and ACE −/− mice (filled bars). The values are mean±SEM (n=7 per group), ***p<0.001.

Food intake was similar (FIG. 18A), but water consumption of the ACE (−/−) mice was more than double that of ACE (+/+) mice ($p<0.001$; FIG. 18B). The blood leptin level of ACE (−/−)mice tended to be lower than that of ACE (+/+) mice (1.5+/−0.3 vs. 8.1+/−2.8 nmol/l: $F(1,4)$ df=5.60, $p<0.07$, n=3 per group) and was correlated with body fat ($r=0.85$, $p<0.05$).

Bone—No significant differences were observed between ACE (−/−) and ACE (+/+) mice in either proportion of bone mineral content (2.2+/−0.06 vs. 2.1+/−0.05, n=7 per group) or bone mineral density (0.076+/−0.002 vs. 0.078+/−0.001 g/cm$^2$, n=7 per group).

Visualization of Regional Fat Masses by MRI: The bright white areas in proton density-weighted MRI images are fat. Visual comparison of series of axial images demonstrated that adipose tissue was markedly reduced in ACE (−/−) compared to ACE (+/+) mice (FIG. 19). This effect was most noticeable in abdominal fat mass, as indicated by the arrow.

Core Body Temperature, Spontaneous Physical Activity Level and Fat Excretion: No significant differences were observed between ACE (−/−) and ACE (+/+) mice in core body temperature (FIG. 20A), spontaneous activity (average distance run, FIG. 20B; speed, FIG. 20C), or proportion of fat in the faecal matter (FIG. 20D).

Hematocrit and Plasma Composition: In Comparison to ACE (+/+) mice, the ACE (−/−) mice had a lower hematocrit ($p<0.001$). No differences were observed in plasma glucose, triglyceride (TG) or total cholesterol levels (Table 12).

Conclusion

Given the same physiological changes occurred using ACE deficient animal models and various polyphenol sources (tea, molasses and molasses extracts), the results support the inference that the polyphenols are acting via an ACE inhibiting mechanism.

The word 'comprising' and forms of the word 'comprising' as used in this description and in the claims does not limit the invention claimed to exclude any variants or additions.

Modifications and improvements to the invention will be readily apparent to those skilled in the art. Such modifications and improvements are intended to be within the scope of this invention.

The invention claimed is:

1. A method for altering the distribution of body mass by increasing the proportion of lean mass to fat mass comprising administering to a subject an effective amount of a polyphenol-containing extract of molasses.

2. The method according to claim 1, wherein the extract has a high antioxidant activity.

3. The method according to claim 1, wherein the effective amount is 1 to 2% by weight of total food consumed.

4. The method according to claim 1, wherein the effective amount for a human is 2 to 20 g/day.

5. The method according to claim 1, wherein the increase in the proportion of lean mass to fat mass of a human suffering cachexia is at least 1 to 2%.

6. The method of claim 1, wherein the subject is a human.

7. The method of claim 6, wherein the human is afflicted with a disease selected from the group consisting of cachexia, diabetes, cancer, Alzheimers, bulimia nervosa, and anorexia.

8. The method of claim 6, wherein the human is afflicted with cachexia and the effective amount is effective to increase the proportion by at least 1%.

9. The method of claim 6, wherein the human is obese.

10. The method of claim 1, wherein the extract is enriched in polyphenols, relative to the molasses from which it was extracted.

* * * * *